US012605541B2

(12) United States Patent
Yan et al.

(10) Patent No.: US 12,605,541 B2
(45) Date of Patent: Apr. 21, 2026

(54) STABILIZED ANTI-CANCER COLD ATMOSPHERIC PLASMA (CAP)-STIMULATED MEDIA AND METHODS FOR PREPARING AND USING SAME

(71) Applicant: The George Washington University, Washington, DC (US)

(72) Inventors: Dayun Yan, Ashburn, VA (US); Michael Keidar, Baltimore, MD (US); Jonathan Sherman, Potomac, MD (US)

(73) Assignee: THE GEORGE WASHINGTON UNIVERSITY, Washington, DC (US)

( * ) Notice: Subject to any disclaimer, the term of this patent is extended or adjusted under 35 U.S.C. 154(b) by 932 days.

(21) Appl. No.: 17/643,342

(22) Filed: Dec. 8, 2021

(65) Prior Publication Data

US 2022/0168565 A1 Jun. 2, 2022

Related U.S. Application Data

(63) Continuation of application No. 15/767,313, filed as application No. PCT/US2016/058741 on Oct. 26, 2016, now abandoned.

(60) Provisional application No. 62/247,223, filed on Oct. 28, 2015.

(51) Int. Cl.
| | |
|---|---|
| A61N 1/36 | (2006.01) |
| A61B 18/04 | (2006.01) |
| A61M 35/00 | (2006.01) |
| A61M 37/00 | (2006.01) |
| A61N 1/00 | (2006.01) |
| A61N 1/44 | (2006.01) |
| H05H 1/24 | (2006.01) |

(52) U.S. Cl.
CPC ....... *A61N 1/36002* (2017.08); *A61M 35/003* (2013.01); *A61M 37/00* (2013.01); *A61N 1/00* (2013.01); *A61N 1/44* (2013.01); *A61B 18/042* (2013.01); *H05H 1/2431* (2021.05); *H05H 1/245* (2021.05); *H05H 1/2465* (2021.05); *H05H 2240/20* (2013.01); *H05H 2245/32* (2021.05); *H05H 2277/10* (2013.01); *H05H 2277/12* (2013.01)

(58) Field of Classification Search
CPC ...................... A61N 1/36002; H05H 2240/20
See application file for complete search history.

(56) References Cited

PUBLICATIONS

Adachi et al., Plasma-activated medium induces A549 cell injury via a spiral apoptotic cascade involving the mitochondrial-nuclear network, Free Radical Biology and Medicine 79 (2015) 28-44 (Year: 2014).*

Haertel et al., Non-Thermal Atmospheric-Pressure Plasma Possible Application in Wound Healing, Biomol Ther 22(6), 477-490 (2014) (Year: 2014).*
Utsumi et al., Selective cytotoxicity of indirect nonequilibrium atmospheric pressure plasma against ovarian clear-cell carcinoma, SpringerPlus 2014, 3:398 (Year: 2014).*
Solé-Martí et al., Plasma-Conditioned Liquids as Anticancer Therapies In Vivo: Current State and Future Directions. Cancers 2021, 13, 452. (Year: 2021).*
Utsumi et al., Effect of Indirect Nonequilibrium Atmospheric Pressure Plasma on Anti-Proliferative Activity against Chronic Chemo-Resistant Ovarian Cancer Cells In Vitro and In Vivo. PLoS ONE 8(12): e81576. (2013) (Year: 2013).*
Hanigan et al. Depleting cysteine: A novel approach to tumor therapy. [abstract]. In: Proceedings of the 106th Annual Meeting of the American Association for Cancer Research; Apr. 18-22, 2015; Philadelphia, PA: AACR; Cancer Res 2015;75(15 Suppl): Abstract nr 4546 (Year: 2015).*
Fu et al., "Selective Amino Acid Restriction Targets Mitochondria to Induce Apoptosis of Androgen-Independent Prostate Cancer Cells", 2006, Journal of Cellular Physiology 209, p. 522-534.
Glover et al., "Interaction of Phenol Red with Estrogenic and Antiestrogenic Action on Growth of Human Breast Cancer Cells ZR-75-1 and T-47-D", 1988, Cancer Research 48, p. 3693-3697.
Kawasaki et al. "Control of the area irradiated by the sheet-type plasma jet in atmospheric pressure," Journal of Physics: Conference Series, vol. 518, 2014, 012016, pp. 1-6.
Keidar, "Plasma for cancer treatment," Plasma Sources Science and Technology, vol. 24, pp. 1-20; May 20, 2015 (Year: 2015).
Kim et al., "Measurement of Reactive Hydroxyl Radical Species Inside the Biosolutions During Non-thermal Atmospheric Pressure Plasma Jet Bombardment onto the Solution", Mar. 13, 2014, Plasma Chemistry and Chemical Processing 34, p. 457-472.
Lewinska et al. "Total anti-oxidant capacity of cell culture media," Clinical and Experimental Pharmacology and Physiology, vol. 34, Apr. 17, 2007 (Apr. 17, 2007), p. 781-786, entire document, especially abstract, p. 782 col. 2 para 5, p. 785 col. 1 para 3.
Mohades et al. "Evaluation of the effects of a plasma activated medium on cancer cells," Physics of Plasmas, vol. 22, No. 12, Oct. 1, 2015 (Oct. 1, 2015), 122001, pp. 1-6.
Smolkova et al., "Critical Analysis of Non-Thermal Plasma-Driven Modulation of Immune Cells from Clinical Perspective", Aug. 28, 2020, International Journal of Molecular Sciences, p. 1-24.
Strekalova et al., "Methionine Deprivation Induces a Targetable Vulnerability in Triple-negative Breast Cancer Cells by Enhancing TRAIL Receptor-2 Expression", Jun. 15, 2015, Clinical Cancer Research 21 (12), p. 2780-2791.
Tanaka et al. "Dynamic behaviour of glioblastoma cells in plasma-activated medium," 22nd International Symposium on Plasma Chemistry, Jul. 5-10, 2015, pp. 1-3.
Ye et al. "Plasma-activated medium suppresses choroidal neovascularization in mice: a new Therapeutic concept for age-related macular degeneration," Scientific Reports, 5, 7705, pp. 1-7, 2015.

(Continued)

*Primary Examiner* — Laura Schuberg
*Assistant Examiner* — Nicholas A Humphries
(74) *Attorney, Agent, or Firm* — BLANK ROME LLP

(57) ABSTRACT

This disclosure relates to stabilized anti-cancer atmospheric plasma (CAP)-stimulated media, to methods for preparing such media, and to methods of treatment using such media.

18 Claims, 18 Drawing Sheets

(56)     References Cited

PUBLICATIONS

Zedda et al., "Morphological and functional changes induced by the amino acid analogue 3-nitrotyrosine in mouse neuroblastoma and rat glioma cell lines", 2004, Neuroscience Letters 363, p. 190-193.
International Search Report issued in PCT/US2016/58741 on Jan. 25, 2017.

\* cited by examiner

STABILIZED ANTI-CANCER COLD ATMOSPHERIC PLASMA (CAP)-STIMULATED MEDIA AND METHODS FOR PREPARING AND USING SAME

This application is a continuation of U.S. patent application Ser. No. 15/767,313, filed Apr. 10, 2018 which is a U.S. national stage of International Application No. PCT/US2016/058741, filed Oct. 26, 2016, which claims the benefit of U.S. Provisional Application No. 62/247,223, filed Oct. 28, 2015, each of which is incorporated by reference in its entirety.

FIELD OF THE INVENTION

The present invention relates to stabilized anti-cancer cold atmospheric plasma (CAP)-stimulated media, to methods for preparing such media, and to methods of treatment using such media.

BACKGROUND OF THE INVENTION

Over the past decade, cold atmospheric plasma (CAP) has shown a selective anti-cancer capacity both in vitro (see, e.g., Refs. 1-8) and in vivo (see, e.g., Refs. 9-13). Various types of CAP devices have been used to directly irradiate cancer cells cultured in the multi-well plates (see, e.g., Refs. 4 and 14), petri-dishes (see, e.g., Refs. 1 and 15), or tumor tissues (see, e.g., Refs. 9 and 12). Recently, plasma-stimulated medium (PSM) has exhibited a significant anti-cancer capacity, as strong as the direct CAP treatment on glioblastoma cells (References 16-18), lung carcinoma cells (see, e.g., Ref 9), and bladder cancer cells (see, e.g., Ref 20). Additionally, it has been reported that microsecond-pulsed plasma-activated media is able to selectively inhibit the growth of lung cancer (H460) cells rather than normal lung cancer (L132) cells (see, e.g., Ref 21). The selective apoptosis in the PSM treated glioblastoma cells (see, e.g., Ref 22), further confirms that PSM is a selective anti-cancer tool. The injection of PSM into mice also significantly inhibits the growth of tumors (see, e.g., Ref 23). PSM may therefore have wide applications in cancer treatment including specific situations where CAP cannot reach deep seated tumors or when the CAP device is not portable.

The CAP-originated reactive species are thought to be the main factor in cancer cell death and growth inhibition (see, e.g., Ref 24). When CAP interacts with the medium, both reactive oxygen species (ROS) such as hydroxyl free radicals (OH) (see, e.g., Ref 25) and hydrogen peroxide (H2O2) (see, e.g., Refs. 19 and 26) and reactive nitrogen species (RNS) such as nitric oxide (NO) (see, e.g., Ref 27) and nitrite (NO2) (see, e.g., Refs. 17 and 28) are dissolved in the aqueous solution. Among them, H2O2 has been found to mainly contribute to the death of cancer cells after the direct CAP irradiation on cancer cells (References 29-31) or the indirect CAP irradiation on the culture medium (see, e.g., Refs. 18 and 19).

For pharmaceutical reasons, PSM should be stable when stored. To date, the largest disadvantage of PSM for future clinical application is its degradation during storage. PSM gradually loses its anti-cancer capacity during storage between room temperature (see, e.g., Refs. 17 and 19) and a few degrees above the freezing point of water (see, e.g., Ref 19).

To date, the sole strategy to inhibit the degradation of PSM during storage is to freeze it at low temperature (−80° C.), However, according to the description of most manufacturers of cell culture media, the ideal storage temperature range for medium is between 2° C. to 8° C., rather than under freezing conditions. Thus, considering the clinical application prospective, PSM should at least be stable at such a temperature range. No method has been reported to date regarding improving the stability of PSM between the recommended storage temperature range of between 2° C. and 8° C.

There is therefore a need for CAP-stimulated medium that exhibit enhanced stability, such that they may be stored at temperatures between, for example, about 2° C. and about 8° C., while retaining its anti-cancer activity.

SUMMARY OF THE INVENTION

The present invention relates to stabilized anti-cancer cold atmospheric plasma-stimulated media (CAPSM), to methods for preparing such stabilized media and to methods treatment using such media. This disclosure not only addresses ways to increase the anti-cancer capacity of CAPSM, but also significantly improve the stability of such media without compromising the CAPSM therapeutic potential in, for example, cancer treatment.

The inventors have found that the degradation of PSM is mainly due to reaction between the plasma-originated reactive species generated during CAP treatment and one or more components in Dulbecco's Modified Eagle Medium (DMEM). Based on this finding, both the reactive species (such as H2O2) in PSM and the anti-cancer capacity of PSM can be significantly stabilized during storage (e.g., at 8° C. and −25° C.) for at least 3 days (such as, e.g., 3-7 days). In addition, the inventors have surprisingly found that addition of, for example, a tyrosine derivative, such as 3-nitro-L-tyrosine, to the medium (e.g. Dulbecco's Modified Eagle Medium, DMEM) can mitigate the degradation of reactive species (such as H2O2) in the media, allowing for the enhanced retention of activity (such as anti-cancer activity), for example, at 8° C. during storage.

Accordingly, in one aspect, the present invention relates to a stabilized cold atmospheric plasma-stimulated media (CAPSM), such as an anti-cancer CAPSM In one embodiment, the CAP-stimulated media comprises phosphate buffered saline (PBS), Dulbecco's Modified Eagle Medium (DMEM), or a combination thereof.

In one embodiment, the CAP-stimulated media comprises phosphate buffered saline (PBS). In another embodiment, the CAP-stimulated media comprises Dulbecco's Modified Eagle Medium (DMEM).

In one embodiment, any of the CAP-stimulated media described herein is stable for a period of up to 7 days, such as up to 6 days, up to 5 days, up to 4 days or up to 3 days, for example, between about I and about 7 days, about I and about 6 days, about I and about 5 days, about I and about 4 days or about I and about 3 days, or for about I day, about 2 days or about 3 days.

In one embodiment, any of the CAP-stimulated media described herein is stable at a temperature of between about −25° C. and about 25° C., such as between about −25° C. and about 22° C., between about 0° C. and about 22° C., between about 0° C. and about 8° C. or between about 2° C. and about 8° C.

In one embodiment, any of the CAP-stimulated media described herein is stable at a temperature of between about −25° C. and about 25° C., such as between about −25° C. and about 22° C., between about 0° C. and about 22° C., between about 0° C. and about 8° C. or between about 2° C. and about 8° C., for a period of up to 7 days, such as up to 6 days, up to 5 days, up to 4 days or up to 3 days, for example, between about I and about 7 days, about I and about 6 days, about I and about 5 days, about I and about 4 days or about I and about 3 days, or for about I day, about 2 days or about 3 days.

In one embodiment, any of the CAP-stimulated media described herein is free of cysteine, or methionine, or a combination thereof.

In one embodiment, any of the CAP-stimulated media described herein Is free of phenylalanine.

In one embodiment, any of the CAP-stimulated media described herein is free of cysteine, or methionine, or phenylalanine, or any combination thereof.

In one embodiment, any of the CAP-stimulated media described herein is free of phenol red.

In one embodiment, any of the CAP-stimulated media described herein is free of cysteine, or methionine, or phenylalanine, or phenol red, or any combination thereof.

In one embodiment, any of the plasma stimulated media described herein comprises glutamine.

In one embodiment, any of the CAP-stimulated media described herein further comprise 3-nitro-L-tyrosine.

In additional embodiments, the 3-nitro-L-tyrosine is present in the CAP-stimulated media at a concentration of up to about 9 mM, such as between about I and about 5 mM, for example, at a concentration of about I mM, about 2 mM, about 3 MM, or about 4 mM.

In another aspect, the present invention relates to a method of (i) stabilizing and/or (ii) enhancing the activity (e.g., anti-cancer activity) of CAP-stimulated stimulated media.

In one embodiment, the method comprises stabilizing the CAP-stimulated media. In one embodiment, the method comprises enhancing the activity of the CAP-stimulated media.

In one embodiment, the method comprises reducing the amount of cysteine, or methionine, or a combination thereof, in the media.

In another embodiment, the method comprises reducing the amount of phenylalanine in the media.

In another embodiment, the method comprises reducing the amount of cysteine, or methionine, or phenylalanine, or any combination thereof, in the media.

In another embodiment, the method comprises reducing the amount of phenol red in the media.

In another embodiment, the method comprises reducing the amount of cysteine, or methionine, or phenylalanine, or phenol red, or any combination thereof, in the media.

In another embodiment, the method comprises adding 3-nitro-L-tyrosine to the media. For example, the 3-nitro-L-tyrosine may be added to the CAP-stimulated media at a concentration of up to about 9 mM, such as between about I and about 5 mM, for example, at a concentration of about I mM, about 2 mM, about 3 MM, or about 4 mM.

In another embodiment, the method comprises (i) reducing the amount of cysteine, or methionine, or phenylalanine, or phenol red, or any combination thereof, in the media and (ii) adding 3-nitro-L-tyrosine to the media.

In another embodiment, the method comprises
(i) reducing the amount of cysteine, methionine, or a combination thereof, in the media;
(ii) reducing the amount of phenylalanine in the media;
(iii) reducing the amount of phenol red in the media;
(iv) adding 3-nitro-L-tyrosine to the media; or
(v) any combination of (i)-(iv).

In another aspect, the present invention relates to a method of treating a target tissue.

In one embodiment, the method comprises administering (e.g., administering to a patient in need of such treatment) a CAP-stimulated media according to any of the embodiments described herein.

In one embodiment, the method comprises treating cancerous and/or precancerous tissue (e.g., cancerous and/or precancerous cells).

In one embodiment, the target tissue comprises lung, bladder, brain or skin tissue (e.g., lung bladder, brain or skin cells), or any combination thereof.

In a further aspect, the present invention related to a method of enhancing the activity (e.g., anti-cancer activity) of CAP-stimulated media, the method comprising (i) increasing the diameter of the well (e.g., in a multi-plate well), and/or (ii) decreasing the gap between the plasma tube and the surface of the media during the CAP-stimulated treatment.

In one embodiment, the method comprises increasing the diameter of the well (e.g., in a multi-plate well) during the treatment. The diameter of the well may be increased by decreasing the number of wells per plate.

In additional embodiments, for example, as the well diameter increases from 11.00 mm (48 wells per plate) to 15.6 mm diameter (24 well per plate), from 15.6 mm to 22.1 mm diameter (12 wells per plate), or from 22.1 mm to 34.8 mm diameter (6 wells per plate), the diameter of the well increases by about 42%, about 42% and about 57%, respectively.

In additional embodiments, for example, as the number of wells per plate decreases from 48 (11.00 mm diameter) to 24 (15.6 mm diameter), from 24 to 12 (22.1 mm diameter), or from 12 to 6 (34.8 mm diameter), the diameter of the well increases by about 42%, about 42% and about 57%, respectively.

In another embodiment, the method comprises decreasing the gap between the plasma tube and the surface of the media during the treatment.

In one embodiment, the gap between the plasma tube and the surface of the media during the treatment is about 4 cm, about 3.5 cm, about 3 cm, about 2.5 cm or about 2 cm. The gap may be decreased from any larger diameter to any lower diameter, as recited herein.

For example, the gap may be decreased from about 4 cm to about 3.5 cm, from about 3.5 cm to about 3 cm, from about 3 cm to about 2.5 cm or from about 2.5 cm to about 2 cm. As a further example, the gap may be decreased from about 4 cm to about 3.5 cm, from about 4 cm to about 3 cm, from about 4 cm to about 2.5 cm or from about 4 cm to about 2 cm.

In additional embodiments, the gap is decreased by about 25%, about 20%, about 17%, or about 14%.

BRIEF DESCRIPTION OF THE DRAWINGS

FIG. 7(a) shows the relative H202 concentration in the CAP-stimulated media. FIG. 7(b) shows the anti-cancer capacity of the CAP-stimulated media on U87MG cells with a confluence of $2 \times 10^4$ cells/mL. FIG. 7(c) shows the anti-cancer capacity of the CAP-stimulated media on MDA-MB-231 cells with a confluence of $2 \times 10^4$ cells/mL. Cells were cultured in 1 mL of the CAP-stimulated media from different multi-well plates. The treatment time was 1 min. Results are presented as the mean±s.d. of three repeated experiments performed in triplicate (a) or in sextuplicate (b and c).

FIGS. 8(a-c) the effect of the gap between the plasma tube and the media surface during the CAP treatment on the H2O2 concentration and anti-cancer capacity of the CAP-stimulated media.

DETAILED DESCRIPTION OF THE INVENTION

Definitions

Unless defined otherwise, all technical and scientific terms used herein generally have the same meaning as commonly understood by one of ordinary skill in the art to which this invention belongs.

The term "comprising" is open ended and, in connection with a composition, refers to the elements recited. The term "comprising" as used in connection with the compositions described herein can alternatively cover compositions "consisting essentially' of or "consisting of" the recited components.

The terms "stable" and "stabilized" as used herein mean, in certain embodiments, that less than about 25%, such as less than about 20%, less than about 15%, less than about IO %, less than about 9%, less than about 8%, less than about 7%, less than about 6%, less than about 5%, less than about 4%, less than about 3%, less than about 2%, less than about I %, less than about 0.5%, or less than about 0.1% of the concentration of the active species (such as $H_2O_2$) in the media decomposes, for example, during a specified period of time at a specified temperature (e.g., when stored between about 2° C. and about 8° C. for at a period of least 3 days (such as, e.g., 3-7 days).

EXAMPLES

The present invention will now be further described by way of the following non-limiting examples. In applying the disclosure of these examples, it should be kept clearly in mind that the examples are merely illustrative of the present invention and should not be construed as limiting the scope of the invention in any way as many variations and equivalents that are encompassed by the present invention will become apparent to those skilled in the art upon reading the present disclosure.

The CAP Device

Figure 1A:
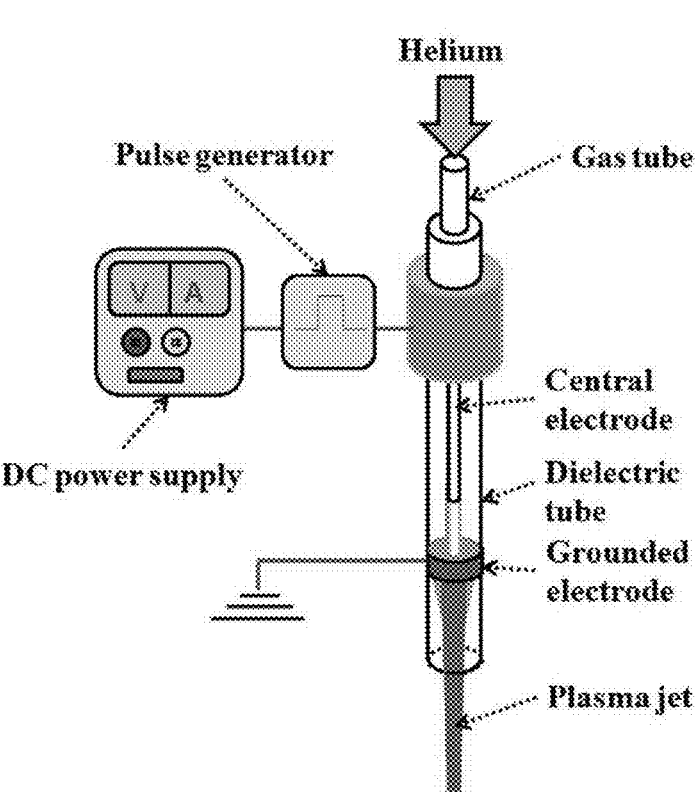
FIG. 1(a) depicts an exemplary CAP device.

The CAP device (FIG. 1a) is a helium CAP jet generator which has been used in a series of studies (see, e.g., Refs. 17, 18 and 32-34). The CAP jet is generated between the central electrode and the grounded ring electrode. The carrying gas is helium with a flow of 4.7 L/min, controlled by a flow meter. The output voltage is 3.16 kV. Any suitable CAP device can be utilized, such as shown in, e.g., International Publication No. WO 12/167089, which is hereby incorporated by reference in its entirety.

Figure 1B:
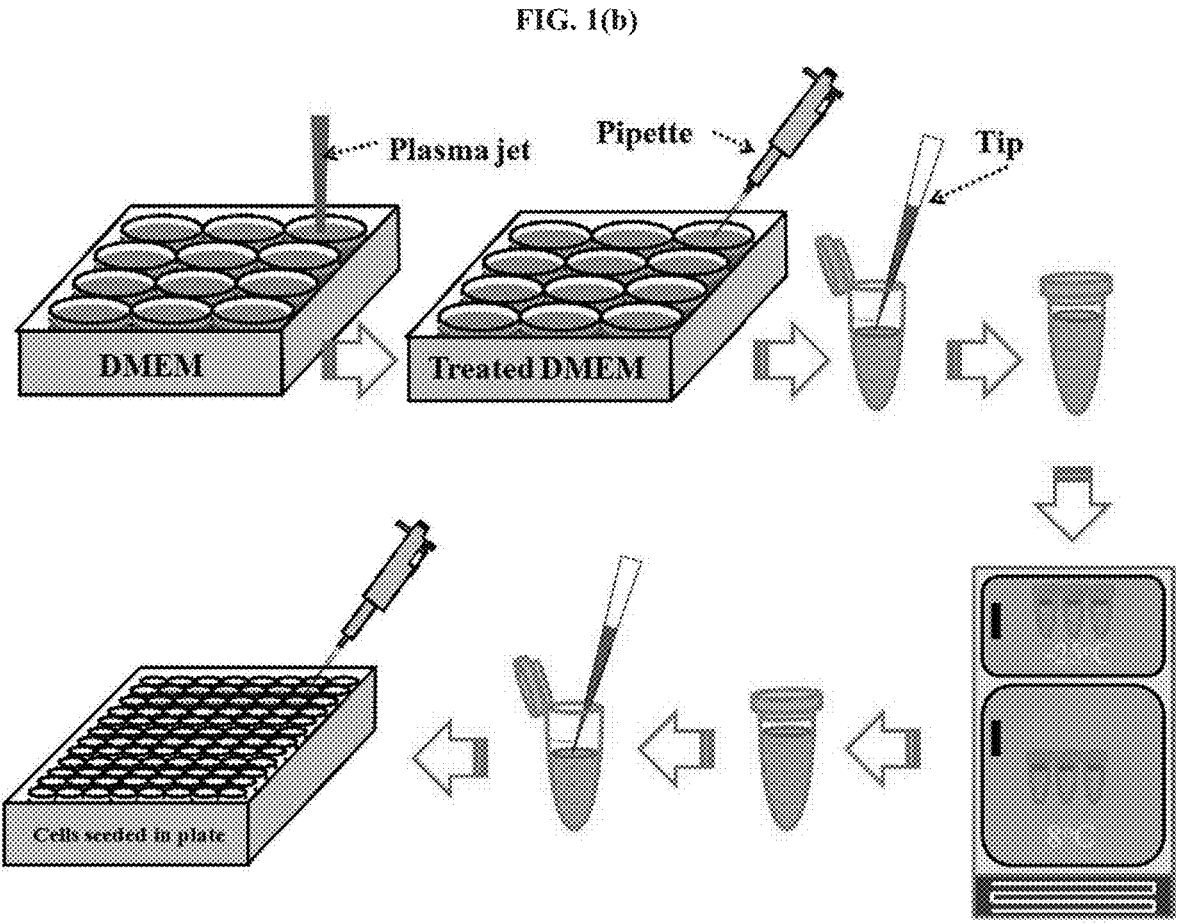
FIG. 1(b) depicts the general research strategy using PSM to affect cancer cells seeded in a multi-well plate.

The general research strategy described herein is illustrated in FIG. 1b. I mL of PSM was made by the vertical irradiation on the medium in a well on a 12-well plate. Then, the PSM was transferred to a 1.5 mL centrifuge tube by pipette. The centrifuge tubes were stored in refrigerators with different internal temperatures (8° C. and –25° C.) for 3 days. Additionally, some centrifuge tubes were stored at 22° C., for the investigation of PSM degradation at room temperature. Ultimately, the PSM was either transferred to culture the seeded cancer cells in a 96-well plate or transferred into a black wall 96-well plate to measure for $H_2O_2$ concentration. Because PBS is not suitable for cell culture, the protocols used to transfer the CAP-stimulated PBS are slightly different from those used to transfer the CAP-stimulated DMEM.

Methods

Medium and Cell Cultures

Standard Dulbecco's modified Eagle's medium (11965-118), modified cysteine/methionine/glutamine-free DMEM (21013-024), modified arginine/lysine/glutamine-free DMEM (A1443 1-01) and PBS (14040-133) were purchased from Thermo Fisher Scientific (Waltham, MA). All DMEM and PBS were mixed with 1% (v/v) antibiotic (penicillin and streptomycin) (Thermo Fisher Scientific) before any experiments were performed. Human glioblastoma (U87MG) cells, pancreatic cancer (PA-TU-8988T) cells and human breast cancer (MDA-MB-231) cells were obtained from George Washington University. All cancer cell lines were seeded with a confluence of $3 \times 10^4$ cells/mL and a volume of 100 μL in each well on a 96-well plate and were cultured for 6 hours in a complete media composed of Dulbecco's modified Eagle's medium supplemented with 10% (v/v) fetal bovine serum (Thermo Fisher Scientific). and 1% (v/v) antibiotic (penicillin and streptomycin) solution under standard cell culture conditions (a humidified, 37° C., 5% $CO_2$ environment). In each experiment, 6 wells in a single column on the 96-well plate were seeded with cancer cells.

Preparation of CAP-Stimulated PBS and DMEM

The protocols to prepare PSM are the same among different experiments. 1 mL of PBS or DMEM (or modified DMEM, such as cysteine/methionine-free DMEM) in a well on a Coming™ Falcon™ 12-well plate was treated by CAP for 1 or 2 minutes. The gap between the end of dielectric plasma tube and the bottom of 12-well plate was 3 cm.

Preparation of $H_2O_2$ Containing PBS and DMEM $H_2O_2$ containing PBS and $H_2O_2$ containing DMEM were prepared by adding 30 wt¾ $H_2O_2$ solution to PBS and DMEM, respectively. The $H_2O_2$ concentration in the $H_2O_2$ containing PBS and $H_2O_2$ containing DMEM were the same as the $H_2O_2$ concentration in the CAP-treated (for 1 minute) 1 mL of PBS or DMEM in the 12-well plate, respectively.

Preparation of Specific Component Containing PBS and DMEM

The amino acid(s) containing PBS, calcium containing PBS, magnesium containing PBS, glucose containing PBS, phenol red containing PBS, and amino acid(s) containing DMEM were prepared by adding and dissolving specific amino acid(s), calcium chloride solution, magnesium chloride solution, D-glucose, phenol red solution or an amino acid derivative (such as 3-nitro-L-tyrosine) in PBS and DMEM, respectively. With the exception of PBS and DMEM, the added components were purchased from Sigma Aldrich.

Affecting the Growth of Cancer Cells Seeded in a 96-Well Plate by CAP-Stimulated DMEM or PBS First, the initial culture medium which had been cultured cells for 6 hours was removed before this step. Then, for the CAP-stimulated DMEM, 100 μL of treated DMEM was transferred from a well on the 12-well plate (or other tubes stored in a refrigerator) to a well on the 96-well plate, in which $3 \times 10^3$ cancer cells were seeded and had been cultured for 6 hours. In each experiment, 6 wells in a single column on the 96-well plate were seeded with cancer cells. In the control group, the DMEM used to culture cancer cells was the untreated DMEM. For the CAP-stimulated PBS, 100 µL of untreated DMEM was first transferred into the well seeded with 3×103 cancer cells on the 96-well plate. Then, 100 µL of treated PBS was transferred into the well which contained 100 µL of untreated DMEM and 3×103 cancer cells. Thus, after this step, the total volume of the mixed medium in each well seeded with cancer cells was 200 µL. For the control group, the PBS transferred into the well was not treated. Ultimately, for the above two cases, the cancer cells on the 96-well plate were cultured under a standard cell culture condition (a humidified, 37° C., 5% CO2 environment) for 3 days.

Measuring and Processing Cell Viability

The cancer cells in the 96-well plates were cultured in the 96-well plate under standard cell culture conditions (a humidified, 37° C., 5% CO2 environment) for 3 days. Then, according to the standard protocols provided by manufacturer, the MTT (3-(4,5-dimethylthiazol-2-yl)-2,5-diphenyltetrazolium bromide, Thermo Fisher Scientific) assay was performed as follows. 0.7 mg/mL MTT-DMEM solution was prepared by dissolving MTT powder in standard DMEM. The the DMEM which had been used to culture the treated cells for 72 hours was then removed from wells on 96-well plate. Cells were then cultured in the MTT-DMEM solution under standard culture conditions for 3 hours. In each well, the volume of MTT-DMEM was replaced by 100 µL of 0.4% (v/v) hydrochloric acid containing isopropanol solution. The 96-well plate filled with hydrochloric acid containing isopropanol solution was then read by a Hybrid Technology HI microplate reader (BioTek Instruments, Winooski, VT) at a 570 nm of absorbance. To facilitate the formation of violet solution, the 96-well plate was shook for I min before the treatment. In each independent experiment, 6 wells in a single column on the 96-well plate were seeded with cancer cells for the cell viability test. The average value of measured cell viability from 6 wells was regarded as the cell viability measured from one independent experiment. To facilitate understanding of the data, all data about cell viability shown in the Figures has been normalized to the control group by dividing the measured cell viability of the experimental group by the measured cell viability of the control group. The final data shown in all Figures are the mean±s.d. of the normalized cell viability from three independently repeated experiments.

Measuring H2O2 Concentration.

Figure 2A:
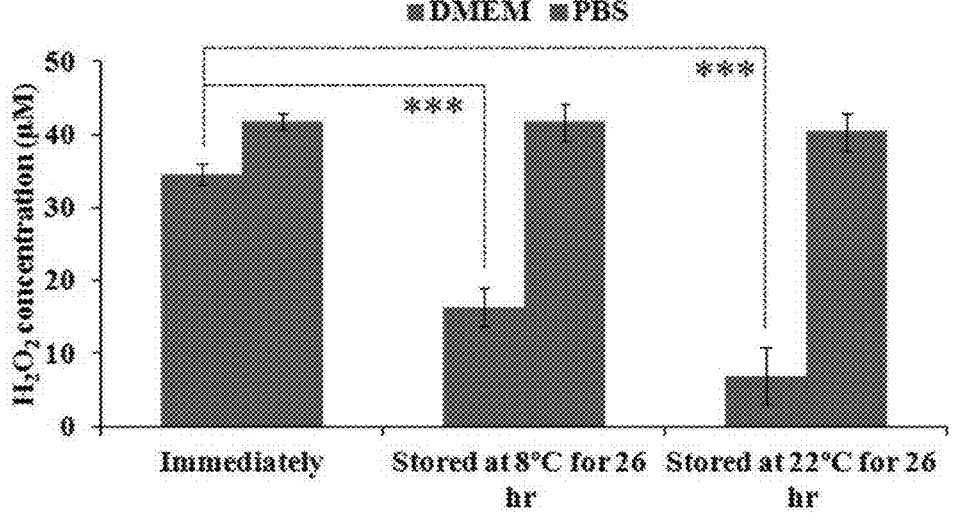
FIG. 2(a) depicts, as described in Example 1, the change of H202 concentration in CAP-stimulated DMEM (left column) and PBS (right column) during storage at 8° C. and 22° C. for 26 hours.
Figure 2B:
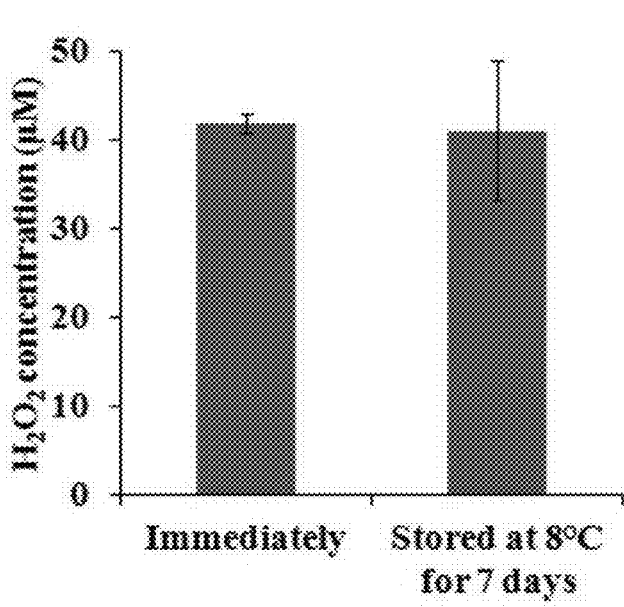
FIG. 2(b) depicts the change of H202 concentration in CAP-stimulated PBS during storage at 8° C. for 7 days.

50 µL of CAP-stimulated medium or PBS to be analyzed for H2O2 concentration was transferred to a well on a black-wall Coming™ Falcon™ 96-well clear bottom plate in triplicate. Subsequently, according to standard protocols provided by Sigma Aldrich (St. Louis, MO), the H2O2 concentration in the cold plasma-stimulated medium was measured as follows. First, 50 µL of red peroxidase substrate stock solution, 200 µL of peroxidase stock solution, and 4.75 ml of assay buffer were mixed to prepare H2O2 probe solution. 50 µL of probe solution was then added in the black 96-well plate and mixed with 50 µL of the CAP-stimulated medium or PBS. After 30 min of storage at the room temperature, with protecting from light, a Hybrid Technology HI microplate reader (BioTek Instruments, Winooski, VT) was used to measure the fluorescence with an excitation wavelength at 540 nm and an emission wavelength at 590 nm. The final measured fluorescent strength of the experimental group was obtained by deducting the measured fluorescence of the control group from the measured fluorescence of the experimental group. The standard H202 solution was used to prepare the standard H202 concentration-fluorescence curve. Based on this standard curve, we obtained the H202 concentration in CAP-stimulated medium or PBS. The triplicate experiments were independently repeated for three times Example I: The Mechanism of PBS Degradation To understand the mechanism of PSM degradation, H202 generation in CAP-stimulated DMEM and PBS after 26 hours of storage (at 8° C. or 22° C.) was compared. As can be seen from FIG. 2, the H202 in the CAP-stimulated PBS was stable during storage. In contrast, most of the H202 in the plasma-stimulated DMEM had been lost after 26 hours storage at either 8° C. or 22° C. (FIG. 2a). The higher storage temperature for PSM, the more degradation occurs in PSM (FIG. 2a). The CAP-stimulated PBS has higher a H202 concentration than the CAP-stimulated DMEM (FIG. 2a).

Figure 2C:
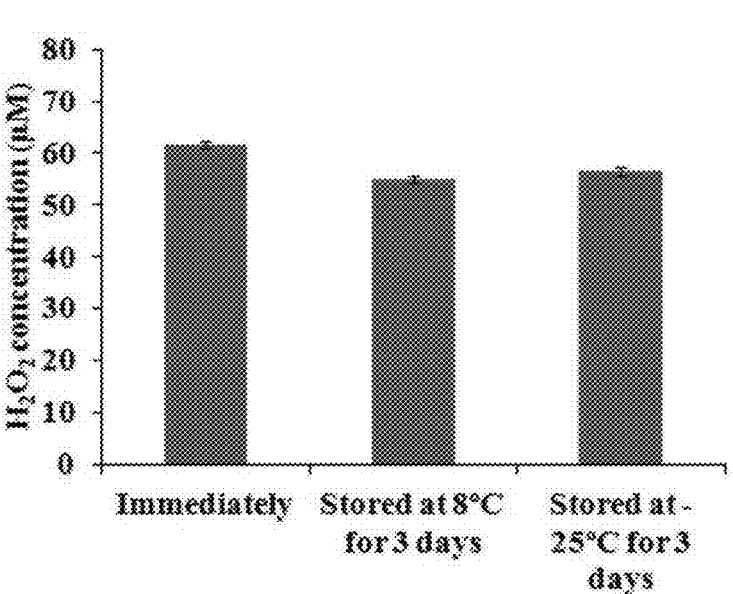
FIG. 2(c) depicts the change of H202 concentration in CAP-stimulated PBS during the storage at 8° C. and –25° C. for 3 days.
Figure 2D:
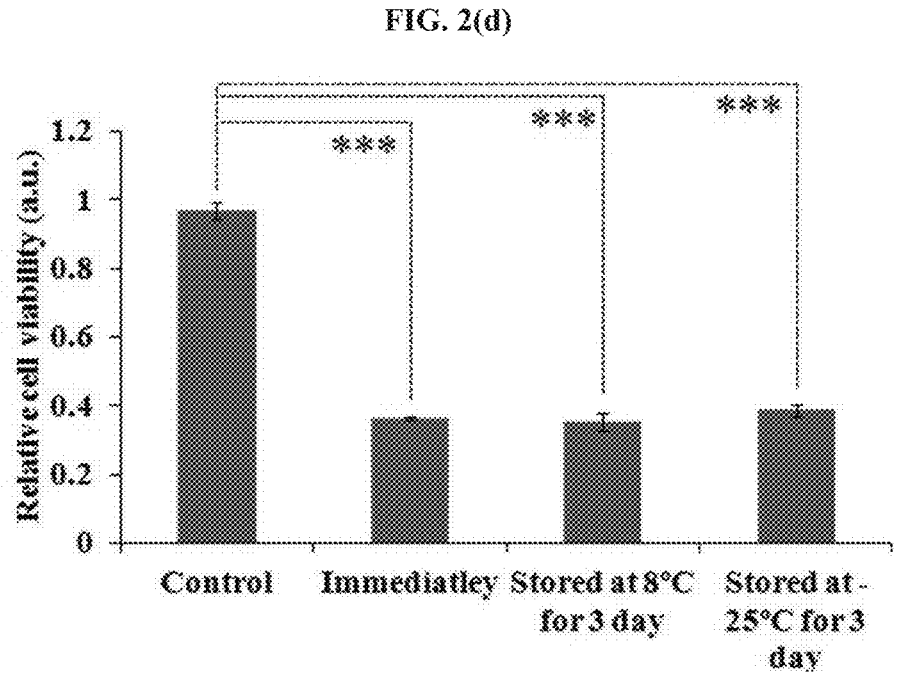
FIG. 2(d) depicts the change of anti-cancer capacity of the CAP-stimulated PBS during storage at 8° C. and –25° C. for 3 days.
Figure 2E:
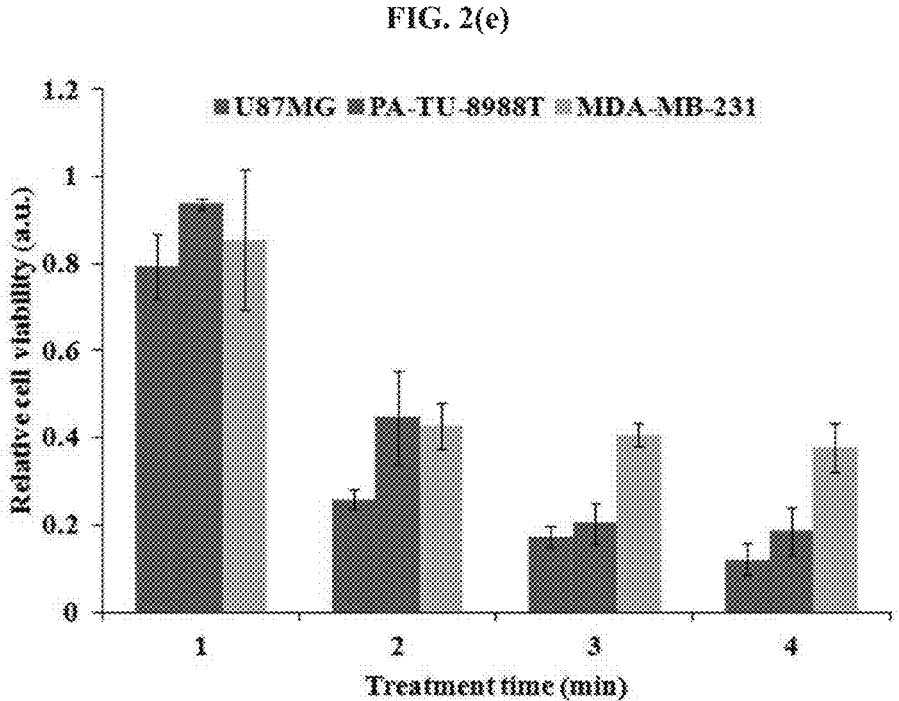
FIG. 2(e) depicts the effect of the cold plasma-stimulated PBS on the cell viability of U87MG (left column), PA-TU-8988T (middle column), and MDA-MB-231 (right column) cells cultured in CAP-stimulated PBS.
Figure 2F:
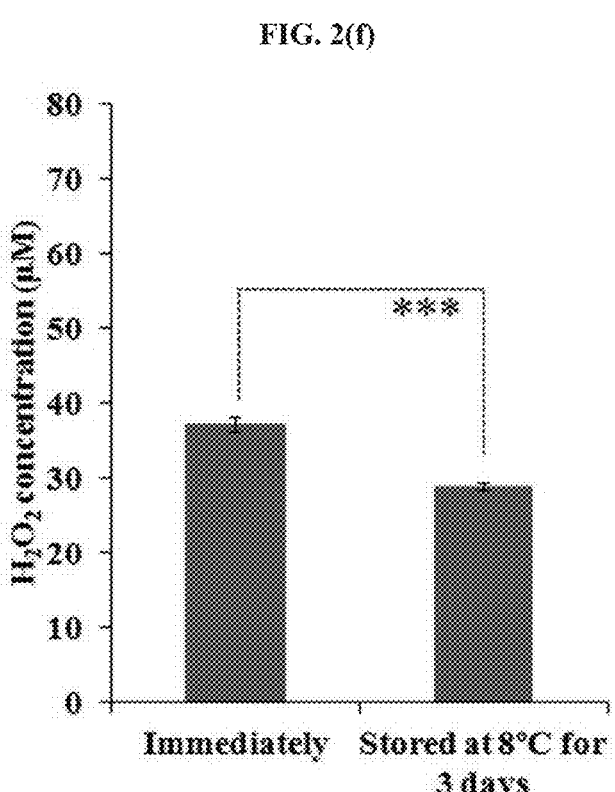
FIG. 2(f) depicts the change of H202 concentration in 37.3 μM H202 containing PBS during the storage at 8° C. for 3 days. The volume of solution for each well was I mL for all experiments. The treatment time for FIGS. 2(a-d) was I minute and 2 minutes, respectively. Results are presented as the mean±standard deviation (s.d.) of three independently repeated experiments performed in triplicate FIGS. (a-c and f) or in sextuplicate FIGS. 2(d and e). For the cell viability, the data have been normalized to corresponding control group. Student's t-test was performed and the significance is indicated as *** p<0.005.

The H202 concentration in the CAP-stimulated PBS was not only stable over 7 days of storage at 8° C. (FIG. 2b) but also stable over 3 days at −25° C. (FIG. 2c). The stable anti-cancer capacity of the CAP-stimulated PBS over 3 days at 8° C. and −25° C. was further confirmed by using the corresponding treated PBS to affect the growth of breast cancer (MDA-MB-231) cells (FIG. 2d). In addition, FIG. 2e shows that that the CAP-stimulated PBS can also effectively inhibit the growth of glioblastoma (U87MG) cells and pancreatic cancer (PA-TU-8988T) cells with a dose-dependent manner, making it a stable anti-cancer PSM over a wide temperature range. As shown in FIG. 2f, the H202 containing PBS experienced a slight degradation over storage at 8° C. for 3 days, which is similar to the slight degradation observed in the CAP-stimulated PBS (FIG. 2c). The H202 in PBS experiences a natural degradation during the storage at 8° C. Thus, the gradual H202 consumption in the cold CAP-stimulated DMEM is likely due to the combined effect of the natural degradation of H202 in aqueous solution and the reaction between H202 and one or more components in the DMEM. The latter mainly controls the degradation at 8° C.

Example 2: The Effect of Components in DMEM on the Degradation of PBS

The effect of several specific components in DMEM on the PSM degradation was also investigated. A comparison between DMEM and PBS reveals that 15 amino acids, glucose, calcium ion, magnesium ion, and phenol red are the main composition differences between DMEM and PBS.

Figure 3A:
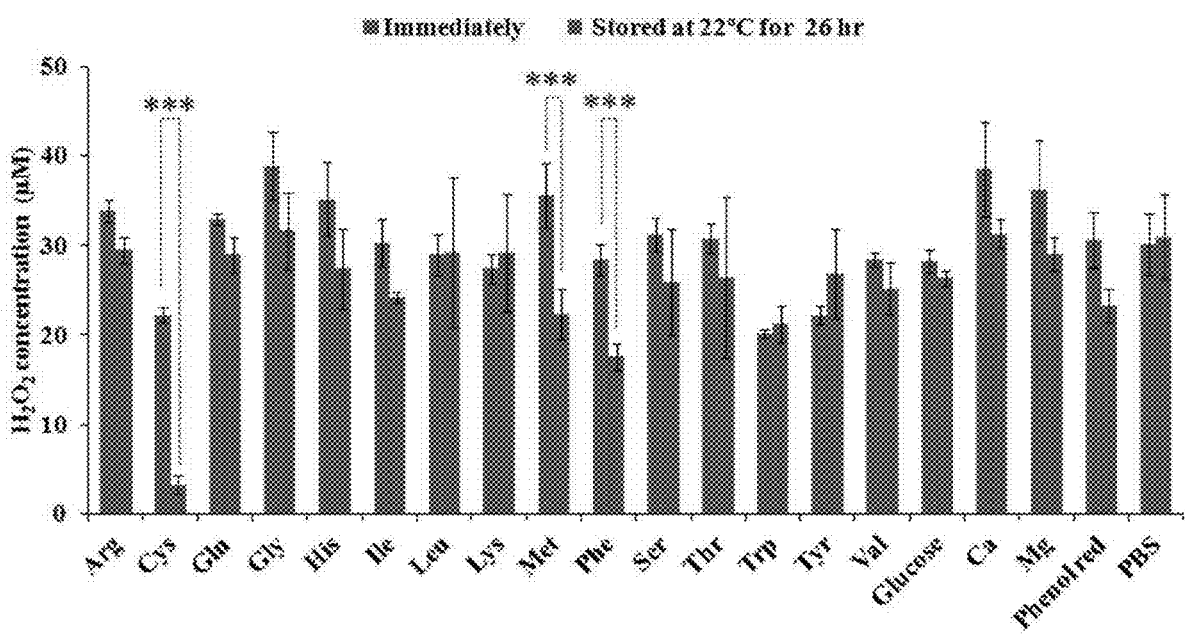
FIG. 3(a) depicts, as described in Example 2, the change of H202 concentration in CAP-stimulated PBS containing specific components in DMEM during the storage at 22° C. for 26 hours (immediately: left column; stored at 22° C. for 26 hours: right column)

Accordingly, 15 specific amino acids solutions, 1 glucose solution, 2 saline solutions (CaCh, MgCh), and 1 phenol red solution were respectively made by adding or dissolving the specific component in PBS according to their concentrations in the standard DMEM. After the CAP treatment and subsequent 26 hours of storage at 22° C., the H202 concentrations in these solutions were measured and compared with the corresponding H202 concentration in the solution immediately following the CAP treatment (FIG. 3a). The H202 in the CAP-stimulated PBS is relatively stable over the storage. In contrast, most of the studied components cause different levels of H202 degradation in the CAP-stimulated PBS-based solution, except tryptophan, tyrosine, and lysine. Cysteine and methionine cause the most significant degradation of the H202 during the storage at room temperature. Phenylalanine also causes noticeable degradation of the H202. Based on these data, a modified DMEM that is free of cysteine, methionine, and/or phenylalanine (or any combination thereof) will be a stable PSM. CAP-stimulated cysteine/methionine/glutamine free DMEM was compared with CAP-stimulated arginine/lysine/glutamine free DMEM and CAP-stimulated standard DMEM. It was found that only the former was stable during storage at 22° C. for 26 hours. The absence of arginine and lysine did not inhibit the H2O2 degradation in PSM. These results are consistent with the trends revealed in FIG. 3a.

Figure 3B:
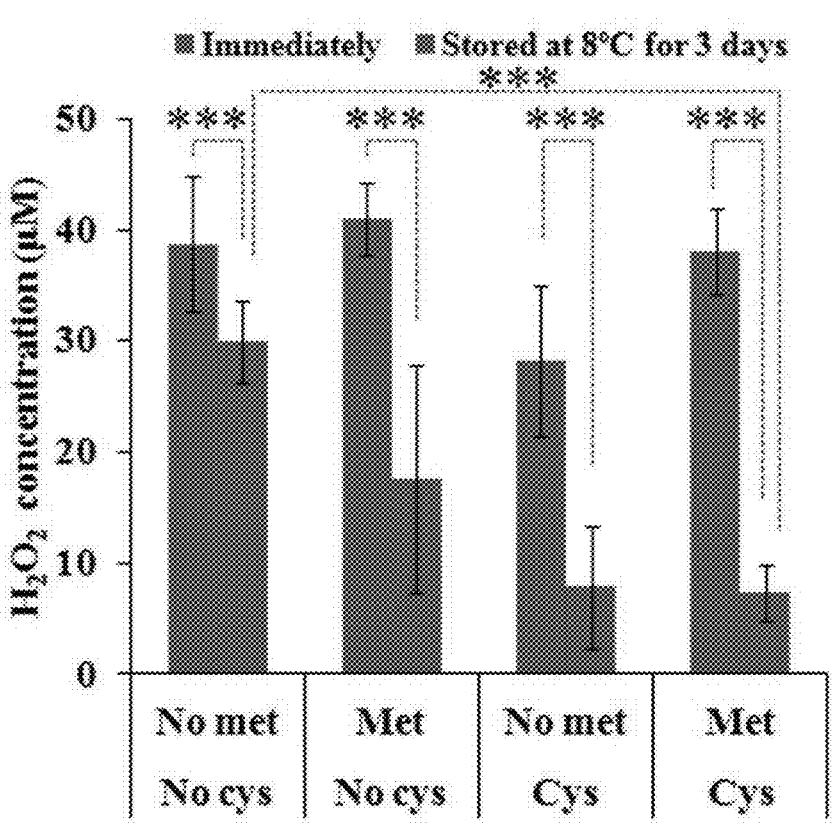
FIG. 3(b) depicts the change of H202 concentration in CAP-stimulated cysteine/methionine-free DMEM, cysteine-free DMEM, methionine-free DMEM, and standard DMEM during storage at 8° C. for 3 days (immediately: left column; stored at 8° C. for 3 days: right column)
Figure 3C:
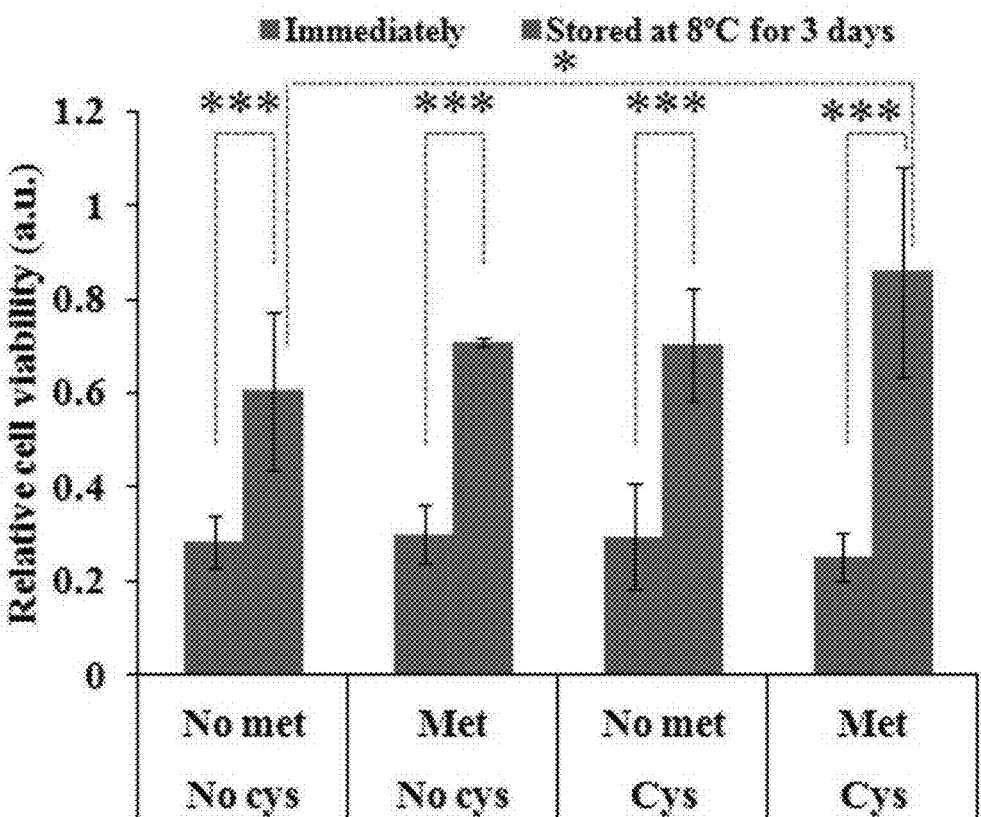
FIG. 3(c) depicts the change of anti-cancer capacity of the CAP-stimulated cysteine/methionine-free DMEM, cysteine-free DMEM, methionine-free DMEM, and standard DMEM during storage at 8° C. for 3 days (immediately: left column; stored at 8° C. for 3 days: right column). For all experiments, the volume of solution and the treatment time in each well was 1 mL and 1 minute. Results are presented as the mean±s.d. of three independently repeated experiments performed in triplicate (a and b) or in sextuplicate (c). For the cell viability, the data have been normalized to corresponding control group. Student's t-test was performed and the significance is indicated as * p<0.05,  p<0.01, * p<0.005.

To prepare DMEM free of both cysteine and methionine, 4 mM glutamine was added to cysteine/methionine/gluta-mine free DMEM. Based on this cysteine/methionine free DMEM, modified DMEM without cysteine (but containing methionine) and modified DMEM without methionine (but containing cysteine) were also prepared as described herein. The effect of cysteine and methionine on the stability of PSM was then investigated. After three days of storage at 8° C., only the CAP-stimulated cysteine/methionine free DMEM showed strong capacity for inhibiting the H2O2 degradation (FIG. 3b). As can also be seen from FIG. 3b, the presence of either cysteine or methionine (or a combination thereof), results in noticeable H2O2 degradation in PSM during storage. The anti-cancer capacity of these PSM on breast cancer (MDA-MB-231) cells was also investigated. In contrast to the experiments performed in the immediately treated media, 3 days of storage at 8° C. causes noticeable degradation of the anti-cancer capacity of PSM, even for the modified DMEM that is free of cysteine and methionine (FIG. 3c). However, compared with other three cases, the cysteine/methionine free DMEM exhibits the strongest capacity to retain the effective species in PSM. Without wishing to be bound by theory, there may be two reasons that the cysteine/methionine free DMEM does not completely inhibit the H2O2 degradation. The first may be that addi-tional components other than cysteine and methionine in DMEM may also contribute to the instability of PSM during the storage (FIG. 3a). Modified DMEM without all these reactive components may be as stable as PBS after the CAP irradiation. The second possibility is that some reactive species other than H2O2 may also contribute to the anti-cancer capacity of PSM.

Figure 4:
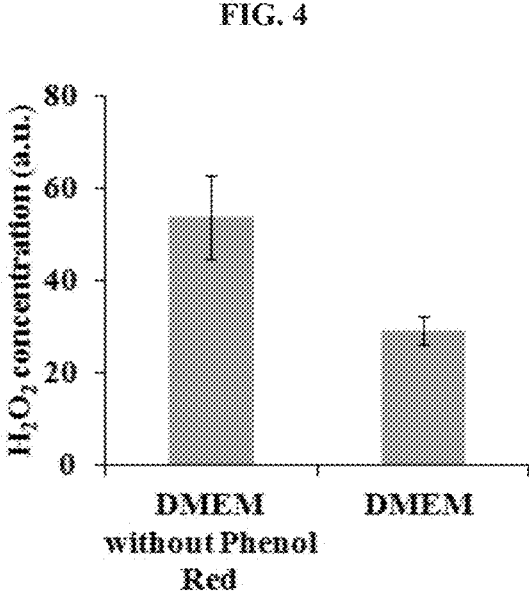
FIG. 4 depicts the effect of phenol red on the H202 concentration in DMEM during CAP treatment. During the CAP treatment, 1 mL of DMEM in 12-well plate was treated by CAP for 1 min. Results are presented as the mean+s.d. of three repeated experiments in triplicate.

FIG. 4 shows the effect of phenol red on the anti-cancer activity of DMEM. As can be seen from FIG. 4, the presence phenol red in the medium significantly consumes H2O2 generated during the CAP treatment. The concentration in the CAP stimulated DMEM without phenol red is nearly 100% greater than that observed in the cap stimulated DMEM containing phenol red. Phenol red acts as a pH value indicator in DMEM, and is not necessary for the growth of cells. Accordingly, for the application of CAPSM, a medium (e.g., DMEM) that is free of phenol red will be more suitable for the application of CAP in cancer treatment.

Example 3: The Effect of Components Under Freezing Conditions

Despite that the typically accepted optimized storage temperature for the culture medium should be between 2 and 8° C., cryopreservation of PSM may still be necessary under certain circumstances. For example, for most refrigerators utilized in pharmacies, the temperature in the freezing chamber is around −20° C. PSM has, however, been found to even further degrade when stored at temperature around −20° C., than when stored at 22° C. (see, e.g., Ref 17) or at 4° C. (see, e.g., Ref 19). A general observation is that freezing aggravates the degradation of PSM. As shown in FIG. 2, both the H2O2 concentration (FIG. 2c) and the anti-cancer capacity (FIG. 2d) of the CAP-stimulated PBS are stably retained during the storage at −25° C. Thus, the degradation of the CAP-stimulated DMEM should also be due to the reaction between components in DMEM and the plasma-originated reactive species, such as H2O2. To verify this, the stability of H2O2 containing DMEM and H2O2 containing PBS under freezing conditions for 3 days was investigated. As seen in FIG. 5, and in contrast to the immediately prepared H2O2 containing DMEM and imme-diately prepared H2O2 containing PBS, H2O2 is completely consumed (Figure Sa) and is well retained (Figure Sb) in the frozen DMEM and the frozen PBS at −25° C., respectively. Accordingly, the plasma-originated (or other source origi-nated) H2O2 naturally tends to strongly react with specific components in DMEM under freezing conditions. In addi-tion, similar to the trend shown in FIG. 2f, H2O2 also shows a natural tendency to be slightly consumed in PBS during the freezing storage. Thus, the degradation of H2O2 in PSM under freezing conditions is likely also due to the reaction between H2O2 and the components in media and a natural degradation in aqueous solution. The former is likely the main factor.

A further investigation was conducted into which com-ponent(s) in DMEM contribute to the degradation of PSM during the freezing storage. This was performed by com-paring the degradation of H2O2 in 15 amino acids solutions, 1 glucose solution, 2 saline solutions (CaCh, MgCh), 1 phenol red solution, and PBS. As shown in Figure Sc, cysteine and methionine remain the two most reactive components in DMEM consuming the plasma-originated H2O2 during the freezing storage. However, in contrast to the trend shown in FIG. 3a, all studied components tend to aggravate the degradation of H2O2 in the cold plasma-stimulated PBS at −25° C., including tyrosine, tryptophan, and lysine, which actually inhibit the degradation of H2O2 in the CAP-stimulated PBS at 8° C. (FIG. 3a). Under freezing conditions, the H2O2 degradation in the methionine solution is stronger than that in the cysteine solution.

Figure 5A:
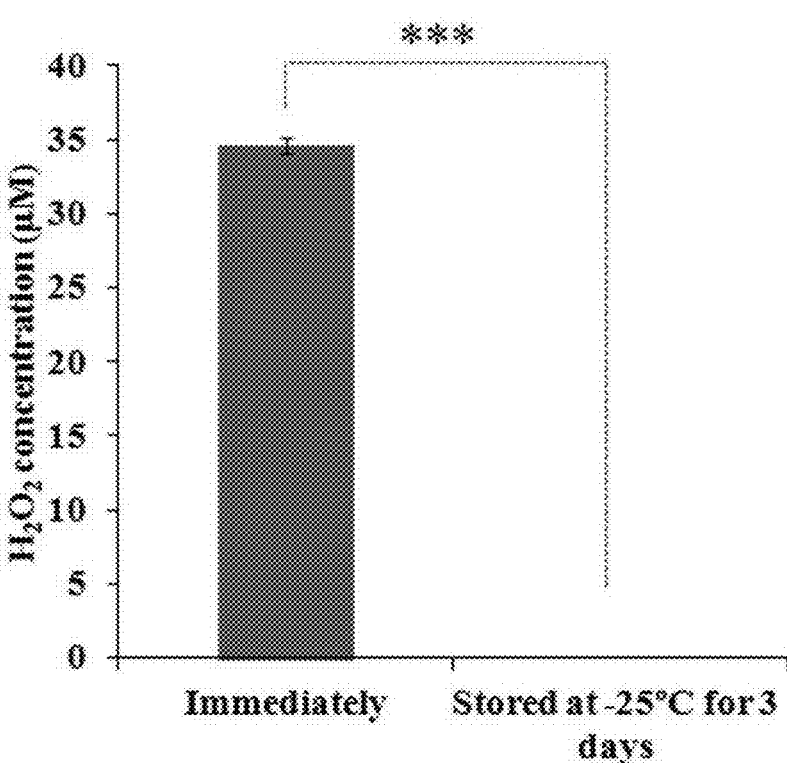
FIG. 5(a) depicts, as described in Example 3, the change of H202 concentration in 34.5 μM H202 containing DMEM during storage at –25° C. for 3 days.
Figure 5B:
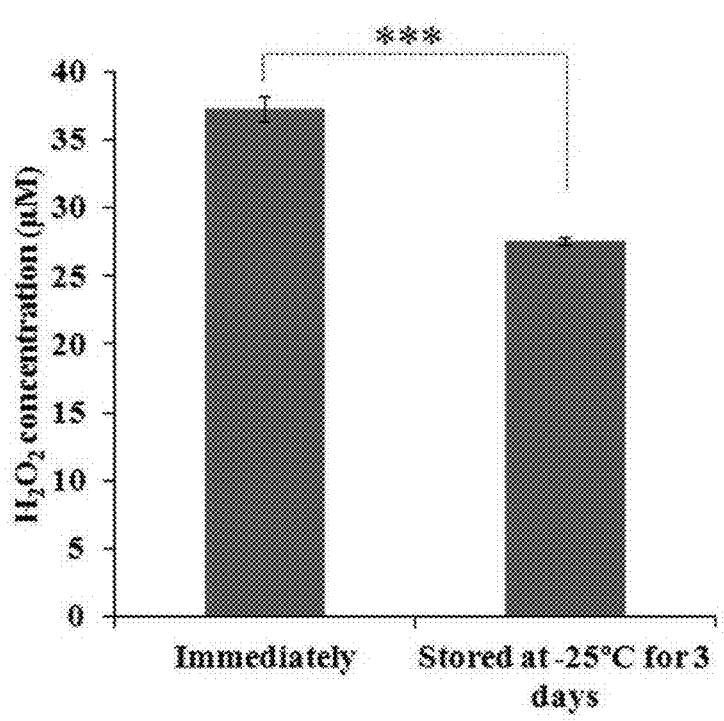
FIG. 5(b) depicts the change of H202 concentration in 37.3 μM H202 containing PBS during storage at –25° C. for 3 days.
Figure 5C:
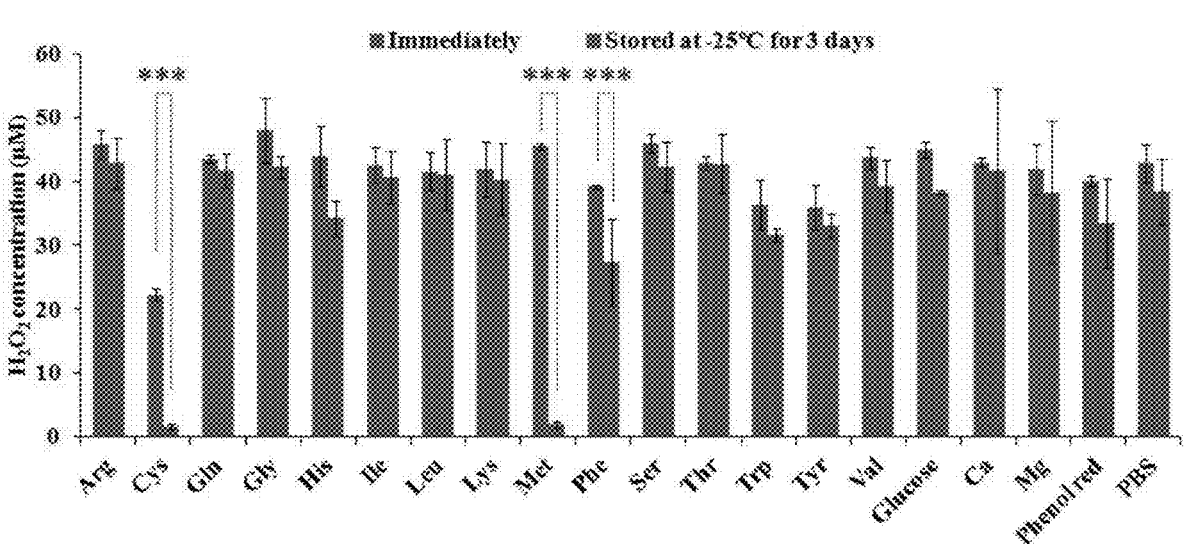
FIG. 5(c) depicts the change of H202 concentration in CAP-stimulated PBS containing specific component(s) in DMEM during storage at –25° C. (immediately: left column; stored at –25° C.: right column)
Figure 5D:
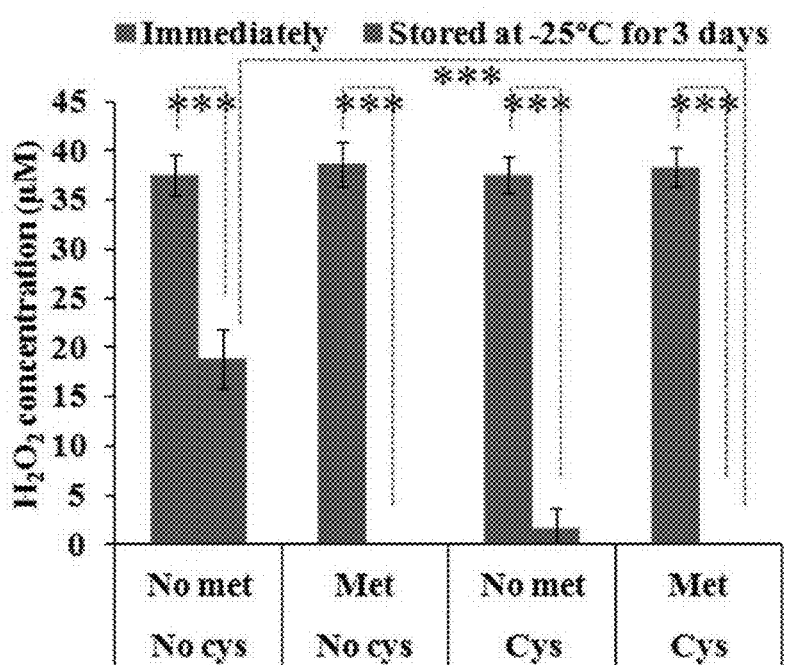
FIG. 5(d) depicts the change of H202 concentration in CAP-stimulated cysteine/methionine-free DMEM, cysteine-free DMEM, methionine-free DMEM, and standard DMEM during storage at –25° C. for 3 days (immediately: left column; stored at –25° C. for 3 days: right column)
Figure 5E:
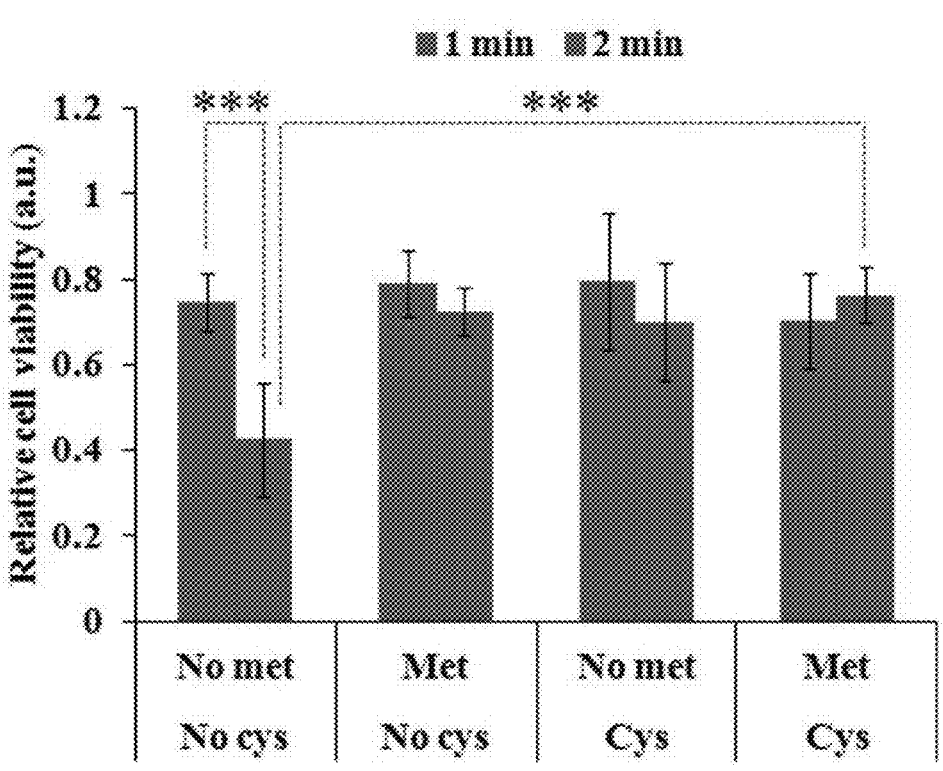
FIG. 5(e) depicts the anti-cancer capacity of CAP-stimulated cysteine/methionine-free DMEM, cysteine-free DMEM, methionine free DMEM, and standard DMEM during storage at –25° C. for 3 days (1 minute: left column; 2 minutes: right column). For all experiments, the volume of solution in each well was 1 mL. The treatment time was 1 minute (c and d). Results are presented as the mean±s.d. of three independently repeated experiments performed in triplicate (a-d) or in sextuplicate (e). For the cell viability, the data have been normalized to corresponding control group. Student's t-test was performed and the significance is indicated as *** p<0.005.

The anti-degradation effect of the cysteine/methionine-free DMEM under freezing conditions using the above mentioned methods was also investigated. The appearance of either of cysteine and methionine in DMEM will result in the complete consumption of H2O2 after 3 days of storage at −25° C. (FIG. 5d). Cysteine-free DMEM is slightly more resistant to degradation of the H2O2 than methionine-free DMEM, which is consistent with the trend revealed in Figure Sc that methionine is more reactive with H2O2 than cysteine during the freezing storage. For the cysteine/me-thionine-free DMEM, more than half of the H2O2 has been consumed during the 3 days of storage at −25° C., which is also consistent with trend shown in Figure Sc that many other components in DMEM also contribute to the instabil-ity of PSM. Ultimately, the anti-cancer capacity of these modified DMEM on MDA-MB-231 cells was compared. When the CAP treatment time is just 1 minute (Figure Se), the difference between the four experimental groups is not pronounced. Such phenomenon may be due to the low concentration of residual H2O2 or reactive species in frozen CAP-stimulated cysteine/methionine-free DMEM, which are too weak to cause a noticeable anti-cancer effect (FIG. 5d). When the CAP treatment time extends to 2 minutes (Figure Se), the appearance of cysteine or methionine, or both, significantly aggravates the degradation of the anti-cancer capacity of PSM. In contrast, the CAP-stimulated cysteine/methionine free DMEM still causes a 60% anti-cancer growth effect.

Example 4: Addition of 3-Nitro-L-Tyrosine

Figures 6A, 6B:
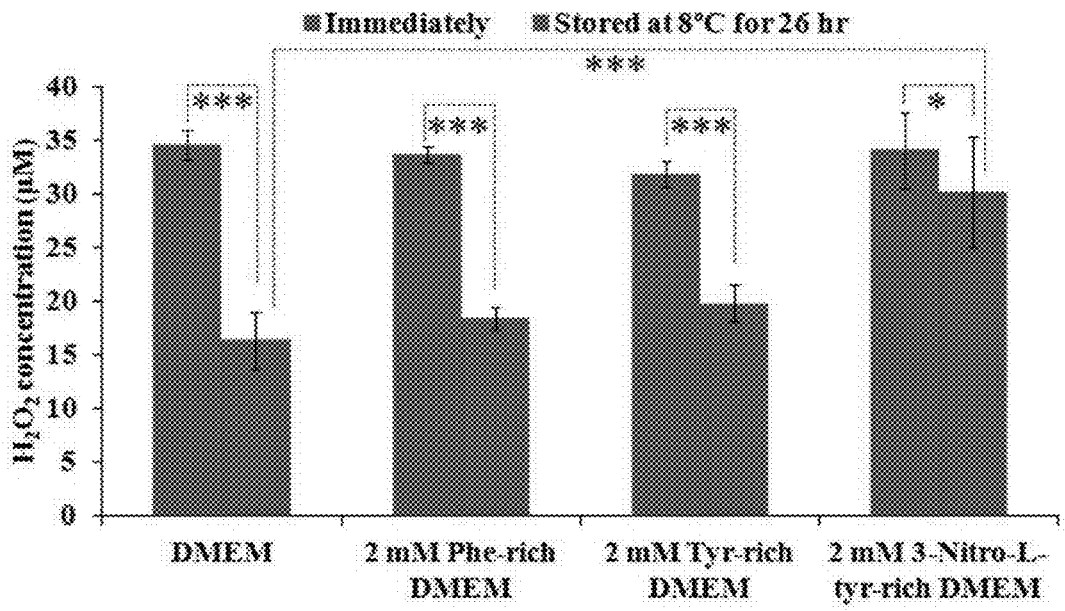
FIG. 6(a) depicts, as described in Example 4, chemical formulas for phenylalanine, tyrosine, and 3-nitro-L-tyrosine.
FIG. 6(b) depicts the change of H202 concentration in CAP-stimulated standard DMEM, phenylalanine-containing DMEM, tyrosine-containing DMEM, and 3-nitro-L-tyrosine containing DMEM during storage at 8° C. for 26 hours (immediately: left column; stored at 8° C. for 26 hours: right column)

Based on the results shown in FIG. 3a, it can be seen that tyrosine increases the H2O2 concentration in CAP-stimulated PBS during storage at 8° C. Among 15 amino acids in DMEM, only tyrosine and phenylalanine have an aromatic ring structures (FIG. 6a). However, phenylalanine causes noticeable H2O2 degradation in the CAP-stimulated PBS during the storage at 8° C. (FIG. 3a). The structural difference between tyrosine and phenylalanine is a hydroxyl substituent on the aromatic ring (FIG. 6a), suggesting that modification of the aromatic ring of an amino acid such as tyrosine may enhances the capacity of the amino acid to inhibit the degradation of H2O2 during storage, e.g., at 8° C.

Figure 6C:
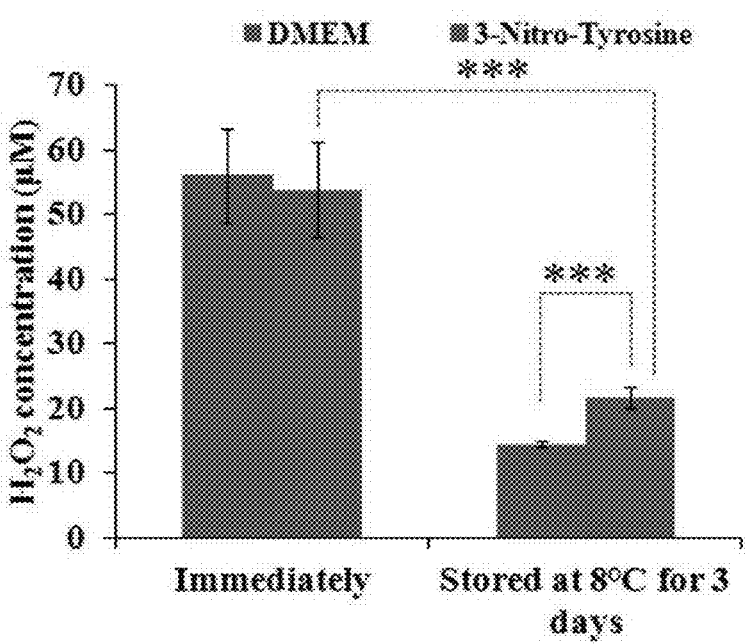
FIG. 6(c) depicts the change of H202 concentration in CAP-stimulated standard DMEM (left column) and 3-nitro-L-tyrosine containing DMEM (right column) during storage at 8° C. for 3 days.
Figure 6D:
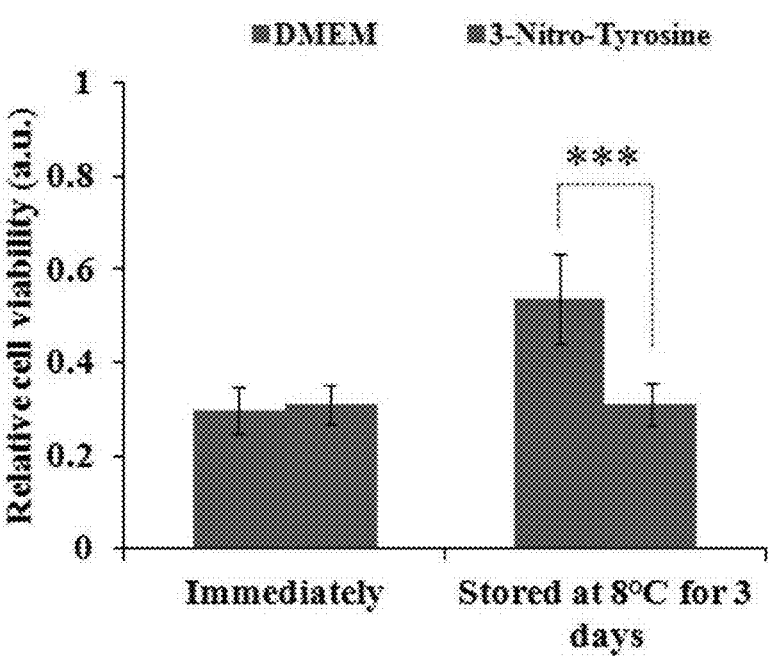
FIG. 6(d) depicts the change of anti-cancer capacity of CAP-stimulated standard DMEM (left column) and 3-nitro-L-tyrosine-containing DMEM (right column) during storage at 8° C. for 3 days.

2 mM 3-nitro-L-tyrosine containing DMEM, 2 mM phenylalanine containing DMEM, and 2 mM tyrosine containing DMEM were prepared by dissolving 3-nitro-L-tyrosine, phenylalanine, and tyrosine powders, respectively, in standard DMEM. Subsequently, the stability of H2O2 in the CAP-stimulated DMEM, tyrosine-containing DMEM, phenylalanine-containing DMEM, and 3-nitro-L-tyrosine-containing DMEM stored at 8° C. were compared. 3-nitro-L-tyrosine significantly inhibits the degradation of H2O2 in PSM (FIG. 6b). In contrast, tyrosine and phenylalanine do not improve the stability of PSM (Figure Sb). Furthermore, it was observed that some H2O2 degradation occurs in the CAP-stimulated 3-nitro-L-tyrosine-containing DMEM and the CAP-stimulated standard DMEM after the storage at 8° C. for 3 days (FIG. 6c). However, despite 60% of plasma-originated H2O2 being lost during storage, the CAP-stimulated 3-nitro-L-tyrosine-containing DMEM is more effective than the CAP-stimulated standard DMEM, in which 74% of plasma-originated H2O2 is lost during the 3 days of storage. Moreover, after storage, the CAP-stimulated 3-nitro-L-tyrosine-containing DMEM still shows a noticeable anti-breast cancer cell capacity as strong as the immediately treated 3-nitro-L-tyrosine-containing DMEM (FIG. 6d). In contrast, the anti-cancer capacity of the CAP-stimulated standard DMEM significantly decays during the storage (FIG. 6d).

Figures 6E, 6F:
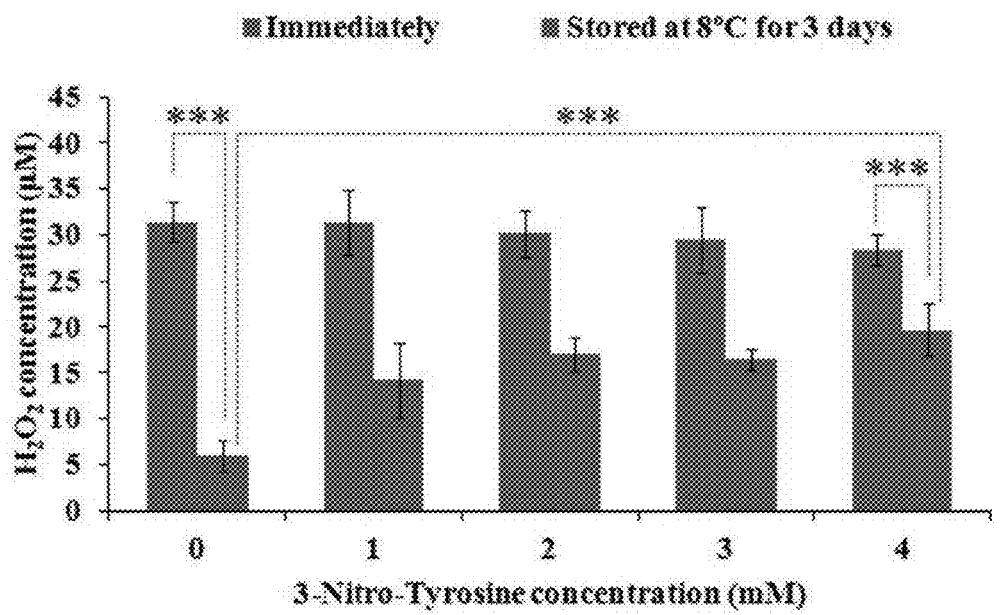
FIG. 6(e) depicts the change of H202 concentration in CAP-stimulated single amino acid containing PBS and double amino acid containing PBS during storage at 22° C. for 26 hours (immediately: left column; stored at 22° C. for 26 hours: right column), the corresponding concentrations of cysteine, methionine, phenylalanine, and 3-nitro-L-tyrosine in PBS were 0.2 mM, 0.2 mM, 0.4 mM and 2 mM, respectively.
FIG. 6(f) depicts the change of H202 concentration in CAP-stimulated 3-nitro-L-tyrosine containing DMEM at different concentrations during storage at 8° C. for 3 days (immediately: left column; stored at 8° C. for 3 days: right column)
Figure 6G:
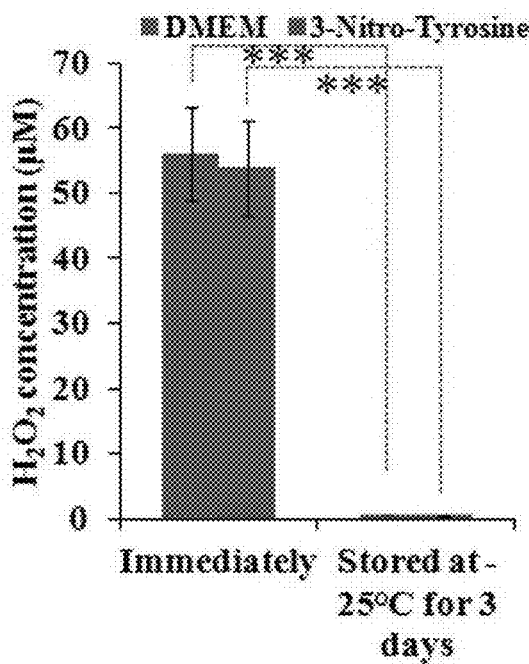
FIG. 6(g) depicts the change of H202 concentration in CAP-stimulated standard DMEM (left column) and 3-nitro-L-tyrosine containing DMEM (right column) during storage at –25° C. for 3 days. For all experiments, the volume of solution in each well was 1 mL. The treatment time was 1 minute for (b, e, and f) and 2 minutes for (c, d, and g). Results are presented as the mean±s.d. of three independently repeated experiments performed in triplicate (b, c, and e-g) or in sextuplicate (d). For the cell viability, the data have been normalized to corresponding control group. Student's t-test was performed and the significance is indicated as * p<0.05,  p<0.01, * p<0.005.

To determine the anti-degradation mechanism of 3-nitro-L-tyrosine in the CAP-stimulated DMEM, it was first investigated whether 3-nitro-L-tyrosine was able to inhibit the H2O2 degradation in 0.2 mM cysteine containing PBS, 0.2 mM methionine containing PBS, and 0.4 mM phenylalanine containing PBS. As shown in FIG. 6e, 2 mM 3-nitro-L-tyrosine is able to completely inhibit the H2O2 degradation in all three CAP-stimulated amino acid containing PBS solutions at 22° C. Accordingly, the CAP-stimulated DMEM may be stabilized by 3-nitro-L-tyrosine through inhibiting the reaction between some components in DMEM (such as, for example, cysteine, methionine and phenylalanine) with the plasma-originated H2O2. The concentration effect of 3-nitro-L-tyrosine on its anti-degradation effect in the CAP-stimulated DMEM was also studied. For the CAP-stimulated 3-nitro-L-tyrosine containing DMEM, the residual H2O2 after 3 days of storage increases as the concentration of 3-nitro-L-tyrosine increases from 1 mM to 4 mM (FIG. 6±). After 3 days of storage at 8° C., 4 mM 3-nitro-L-tyrosine-containing DMEM loses 30% of the H2O2 originated from the CAP treatment. In contrast, the standard DMEM loses 81% of the plasma-originated H2O2 (FIG. 6±). FIG. 6g shows the effect after storage at −25° C. for 3 days.

Example 5: Effect of Well Diameter

Figure 7A:
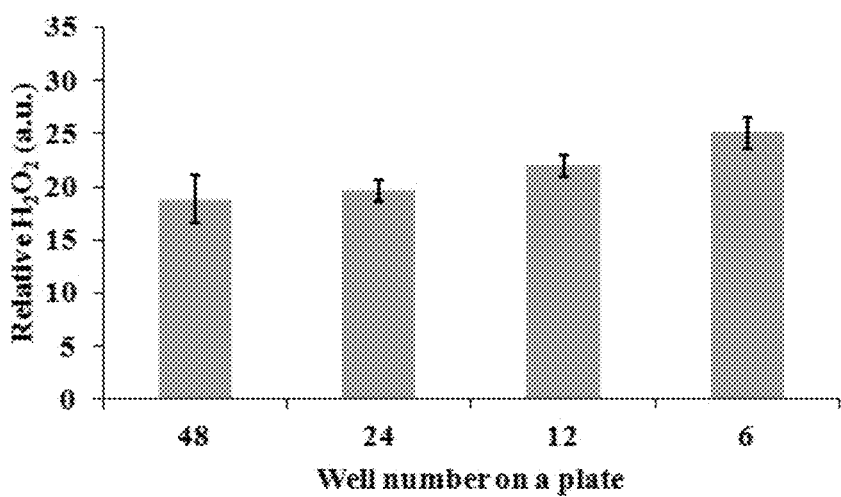
FIGS. 7(a)-(c) depicts the effect of well diameter of the multi-plate well on the H202 concentration and anti-cancer capacity of the CAP stimulated media. The diameter of the well in a 48-well plate, 24-well plate, 12-well plate, and 6-well plate is 11.0 mm, 15.6 mm, 22.1 mm, and 34.8 mm, respectively.
Figure 7B:
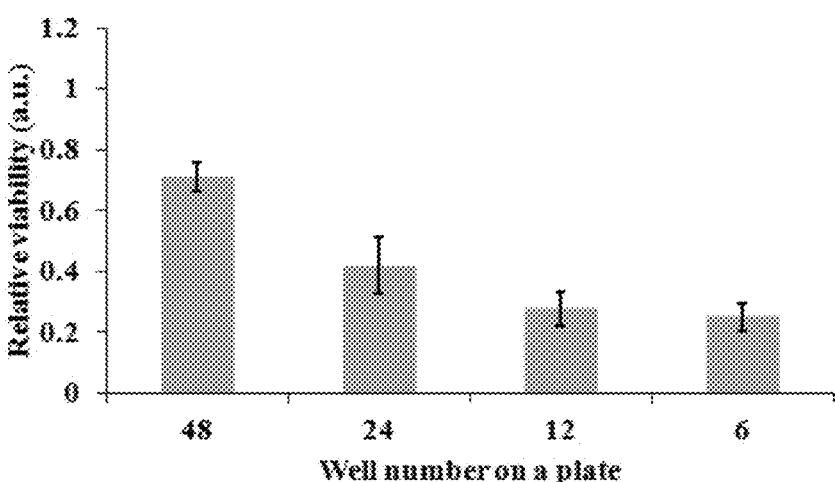
Figure 7C:
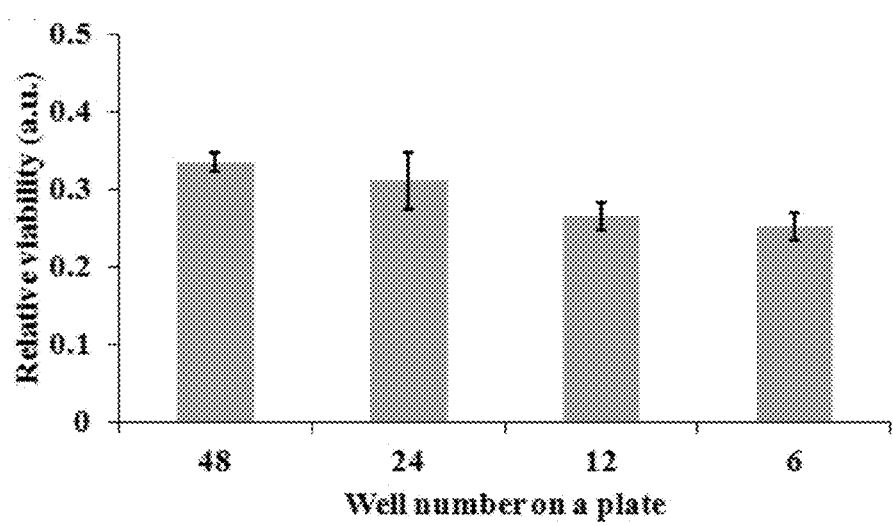

FIG. 7 shows how the H2O2 concentration and the anti-cancer capacity of the CAP-stimulated media (10% FBS+ 90% DMEM) can be controlled by the diameter of well on the multi-well plate used in the CAP treatment. FIG. 7a shows the relative H2O2 concentration in 1 mL of CAPSM. FIGS. 7b and 7c show the relative viability of glioblastoma (U87) cells ($2 \times 10^4$ cells/ml) (FIG. 7b) and breast cancer (MDA-MB-231) cells ($2 \times 10^4$ cells/ml) (FIG. 7c) cultured in 1 mL of CAPSM from different multi-wells plates. The treatment times for (b) and (c) were 1 minute. Cells were then cultured for 3 days before the cell viability measurement. The results are presented as the mean±s.d. of three repeated experiments performed in sextuplicate.

As can be seen from FIG. 7, increasing the diameter of the well on a multi-well plate increases the anti-cancer activity of the CAPSM. The diameter of well in a 48-well plate, 24-well plate, 12-well plate, and 6-well plate is 11.0 mm, 15.6 mm, 22.1 mm, and 34.8 mm, respectively. The anti-cancer capacity (the ratio of the decreased cell viability and the initial cell viability, which is also equal to the difference between 1 and the relative cell viability) of the CAP-stimulated media on U87MG cells increase from about 29% to about 75% as the diameter of well increases from 11.0 mm to 34.8 mm. Similarly, the anti-cancer capacity of the CAP-stimulated media on MDA-MB-231 cells increases from about 67% to about 75% as the diameter of well increases from 11.0 mm to 34.8 mm.

Figure 8A:
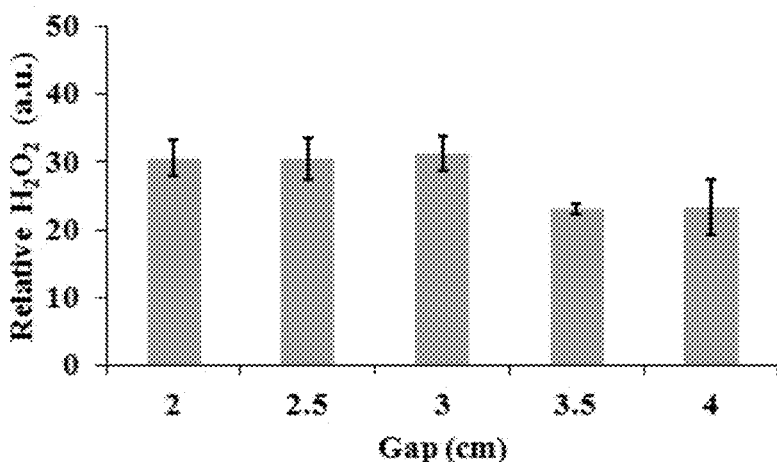
FIG. 8(a) shows the relative H2O2 concentration in 1 mL of the CAP-stimulated media.
Figure 8B:
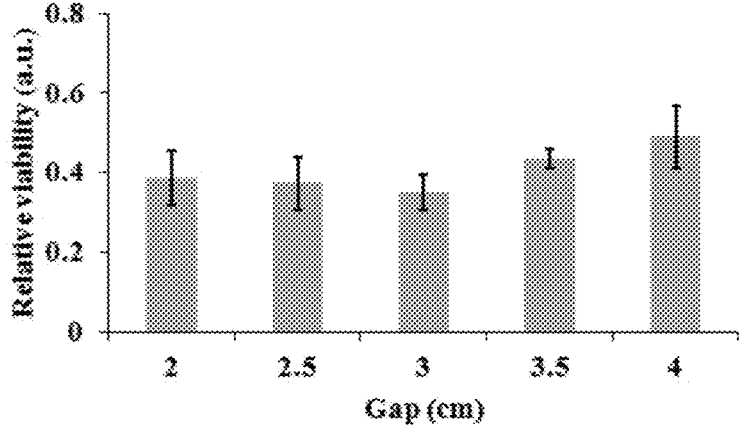
FIG. 8(b) shows the anti-cancer capacity of the CAP-stimulated media on U87MG cells with a confluence of $2 \times 10^4$ cells/mL.
Figure 8C:
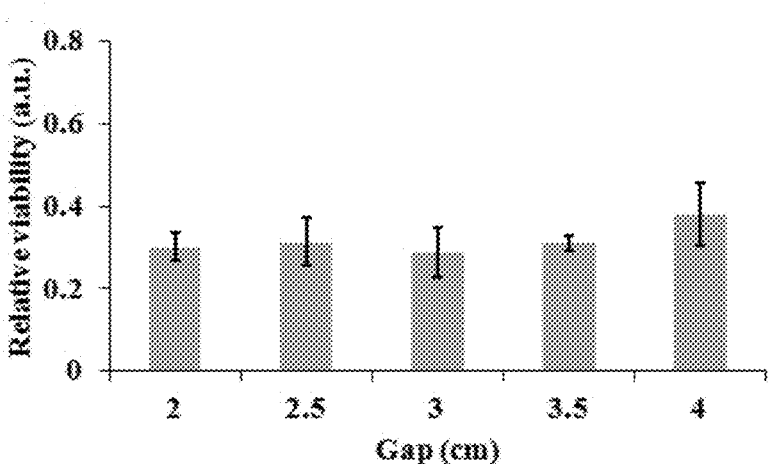
FIG. 8(c) shows the anti-cancer capacity of the CAP-stimulated media on MDA-MB-231 cells with a confluence of $2 \times 10^4$ cells/mL. Cells were cultured in 1 mL of CAP-stimulated media. The treatment time was 1 min. Results are presented as the mean±s.d. of three repeated experiments performed in triplicate (a) or in sextuplicate (band c).

Example 6: Effect of the Gap Distance Between the Plasma Tube and the Medium Surface FIG. 8 shows how the H2O2 concentration and the anti-cancer capacity of the CAP-stimulated media (10% FBS+ 90% DMEM) can be controlled by adjusting the gap between the plasma tube and the surface of media during the CAP treatment. FIG. 8a shows the relative H2O2 concentration in 1 mL of CAPSM. FIGS. 8b and 8c show the relative viability of U87 cells (FIG. 8b) and MDA-MB-231 cells (FIG. 8c) cultured in 1 mL of CAPSM. For all figures, the CAP treatment time was 1 minute. 6-well plates were used during the CAP treatment. The seeding cell confluence was $2 \times 10^4$ cells/ml. Cells were then cultured for 3 days before the cell viability measurement. Results are presented as the mean±s.d. of three repeated experiments performed in sextuplicate.

As can be seen from FIG. 8, decreasing the gap between the plasma tube and the surface of the medium during CAP treatment increases the anti-cancer activity of the CAPSM. The anti-cancer capacity (the ratio of the decreased cell viability and the initial cell viability, which is also equal to the difference between 1 and relative cell viability) of the CAP-stimulated media on U87MG cells increases from about 51% to about 61% as the gap decreases from 4 cm to 2 cm. Similarly, the anti-cancer capacity of the CAP-stimulated media on MDA-MB-231 cells increases from about 62% to about 70% as the gap decreases from 4 cm to 2 cm.

Example 8: Magnetic Resonance Imaging

Figure 9A:
FIGS. 9(a-b) depicts a pre-operative axial post-gadolinium magnetic resonance (MR) image displaying a left temporal glioblastoma (FIG. 9A), and a post-operative axial post-gadolinium MR image displaying a residual line of enhancing tumor (FIG. 9B, light arrow). The surgical resection cavity (dark arrow) is filled with CAPSM (light coloration).
Figure 9B:
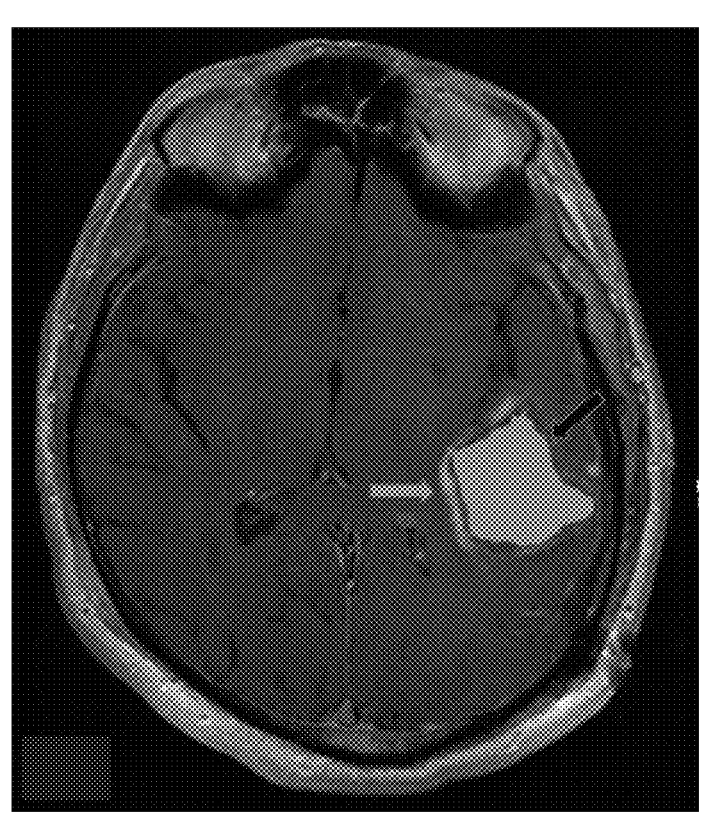

FIG. 9 shows a pre-operative axial post-gadolinium magnetic resonance (MR) image displaying a left temporal glioblastoma (FIG. 9A), and a post-operative axial post-gadolinium MR image displaying a residual line of enhancing tumor (FIG. 9B, light arrow) following direct injection of a CAPSM according to the present disclosure into the brain tumor. The surgical resection cavity (dark arrow) is filled with CAPSM (light coloration).

REFERENCES

The following references may be pertinent to the present disclosure:

1. Fridman et al., Floating electrode dielectric barrier discharge plasma in air promoting apoptotic behavior in melanoma skin cancer cell lines. *Plasma Chem Plasma P.* 27, 163-176, doi: 10.1007/s1 1090-007-9048-4(2007).
2. Keidar, Plasma for cancer treatment. *Plasma Sources Sci T.* 24, 033001-033020, doi: 10.1088/0963-0252/24/3/033001 (2015).
3. Ratovitsk et al., Anti-Cancer Therapies of 21st Century: Novel approach to treat human cancers using cold Atmospheric plasma. *Plasma Process Polym.* 11, 1128-1137, doi: 10.1002/ppap.201400071 (2014).
4. Zhang et al., Ablation of liver cancer cells in vitro by a plasma needle. *Appl Phys Lett.* 93, 0215021-0215023, doi: 10.1063/1.2959735 (2008).
5. Schlegel et al., Plasma in cancer treatment. *Clin Plasma Med* I, 2-7, doi: 10.1016/j.cpme.2013.08.001 (2013).
6. Yan et al., Toward understanding the selective anticancer capacity of cold atmospheric plasma—A model based on aquaporins. *Biointerphases.* IO, 04080101-04080113, doi: 10.1116/1.4938020 (2015).
7. Wang et al., Cold atmospheric plasma for selectively ablating metastatic breast cancer cells. *PloS One.* 8, e7374101-e73741II, doi: 10.1371/joumal.pone.0073741 (2013).
8. Zhu et al., Synergistic effect of cold atmospheric plasma and drug loaded core-shell nanoparticles on inhibiting breast cancer cell growth. *Sci Rep.* 6, 2197401-2197411, doi: 10.1038/srep21974 (2016).
9. Keidar et al., Cold plasma selectivity and the possibility of a paradigm shift in cancer therapy. *Brit J Cancer.* 105, 1295-1301, doi: 10.1038/bjc.2011.386 (2011).
10. Brulle et al., Effects of a non thermal plasma treatment alone or in combination with gemcitabine in a MIA PaCa2-luc orthotopic pancreatic carcinoma model. *PloS One.* 7, e5265301-e5265310, doi: 10.1371/joumal-.pone.0052653 (2012).
11. Vandamme et al., Response of human glioma U87 xenografted on mice to non thermal plasma treatment. *Plasma Med.* I, 27-43, doi: 10.1615/PlasmaMed.v1.i1.30 (2011).
12. Partecke et al., Tissue tolerable plasma (TTP) induces apoptosis in pancreatic cancer cells in vitro and in vivo. *BMC Cancer.* 12, 47301-47310, doi: 10.1186/1471-2407-12-473 (2012).
13. Vandamme et al., ROS implication in a new antitumor strategy based on non-thermal plasma. *Int J Cancer.* 130, 2185-2194, doi: 10.1002/ijc.26252 (2012).
14. Lee et al., Degradation of adhesion molecules of G361 melanoma cells by a non-thermal atmospheric pressure microplasma. *New J Phys.* 11, 11502601-11502613, doi: 10.1088/1367-2630/11/11/1 15026 (2009).
15. Kim et al., Induction of apoptosis m human breast cancer cells by a pulsed atmospheric pressure plasma jet. *Appl Phys Lett.* 97, 02370201-02370203, doi: 10.1063/1.3462293 (2010).
16. Tanaka et al., Plasma-activated medium selectively kills glioblastoma brain tumor cells by down-regulating a survival signaling molecule, AKT Kinase. *Plasma Med.* I, 265-277, doi: 10.1615/PlasmaMed.2012006275 (2011).
17. Yan et al, Controlling plasma stimulated media in cancer treatment application. *Appl Phys Lett.* 105, 22410101-22410104, doi: 10.1063/1.4902875 (2014).

18. Yan, Principles of using cold atmospheric plasma stimulated media for cancer treatment. *Sci Rep.* 5, 1833901-1833901-1 7, doi:10.1038/srep18339 (2015).
19. Adachi et al., Plasma-activated medium induces A549 cell mJury via a spiral apoptotic cascade involving the mitochondrialnuclear network. *Free Radical Bio Med* 79C, 28-44, doi: 10.1016/j.freeradbiomed. 2014.11.014 (2014).
20. Mohades et al., Evaluation of the effects of a plasma activated medium on cancer cells. *Phys Plasmas.* 22, 12200101-12200106, doi: 10.1063/1.4933367 (2015).
21. Kumar et al., The action of microsecond-pulsed plasma-activated media on the inactivation of human lung cancer cells. *J Phys D Appl Phys.* 49, 1 1540101-11540109, doi: 10.1088/0022-3727/49/11/1 15401 (2016).
22. Kurake et al., Cell survival of glioblastoma grown in medium containing hydrogen peroxide and/or nitrite, or in plasma-activated medium. *Arch Biochem Biophys.* available online, doi: 10.1016/j.abb.2016.01.011 (2016).
23. Utsumi et al., Effect of indirect nonequilibrium atmospheric pressure plasma on anti-proliferative activity against chronic chemoresistant ovarian cancer cells in vitro and in vivo. *PloS One.* 8, e8157601-e815760110, doi: 10.1371/joumal.pone.0081576 (2013).
24. Kalghatgi et al., Effects of non-thermal plasma on mammalian cells. *PloS One.* 6, e1627001-e1627011 (2011).
25. Ninomiya et al., Evaluation of extra- and intra-cellular OH radical generation, cancer cell injury, and apoptosis induced by a nonthermal atmospheric-pressure plasma jet. *J Phys D Appl Phys.* 46, 42540101-42540108, doi: 10.1088/0022-3727/46/42/425401 (2013).
26. Ahn et al., Atmospheric-pressure plasma jet induces apoptosis involving mitochondria via generation of free radicals. *PloS One.* 6, e2815401-e2815407 (2011).
27. Ma et al., Non-thermal atmospheric pressure plasma preferentially induces apoptosis in p53-mutated cancer cells by activating ROS stress-response pathways. *PloS One.* 9, e9194701-e9194714, doi: 10.1371/joumal-.pone.0091947(2014).
28. Gibson et al., Interactions of a non-thermal atmospheric pressure plasma effluent with PC-3 prostate cancer cells. *Plasma Process Polym.* 11, 1142-1149, doi: 10.1002/ppap.201400111 (2014).
29. Ahn et al., Targeting cancer cells with reactive oxygen and nitrogen species generated by atmospheric-pressure air plasma. *PloS One.* 9, e8617301-e8617313, doi: 10.1371/joumal.pone.0086173 (2014).
30. Bekeschus et al., Hydrogen peroxide: A central player in physical plasma-induced oxidative stress m human blood cells. *Free Radical Res.* 48, 542-549, doi: 10.3109/10715762.2014.892937 (2014).
31. Kumar et al., Influence of water vapour with non-thermal plasma jet on the apoptosis of SK-BR-3 breast cancer cells. *RSC Adv.* 5, 14670-14677, doi: 10.1039/c4ra15879b (2015).
32. Shashurin et al., Influence of cold plasma atmospheric jet on surface integrin express10n of living cells. *Plasma Process Polym.* 7, 294-300, doi: 10.1002/ppap.200900086 (2010).
33. Volotskova et al., Targeting the cancer cell cycle by cold atmospheric plasma. *Sci Rep.* 2, 63601-63610, doi: 10.1038/srep00636 (2012).
34. Cheng et al., Synergistic effect of gold nanoparticles and cold plasma on glioblastoma cancer therapy. *J Phys D Appl Phys.* 47, 33540201-33540208, doi: 10.1088/0022-3727/47/33/335402 (2014).

35. Takai et al., Chemical modification of amino acids by atmospheric-pressure cold plasma in aqueous solution. *J Phys D Appl Phys.* 47, 28540301-28540315, doi: 10.1088/0022-3727/47/28/285403 (2014).

36. Ishaq et al., Atmospheric gas plasma-induced ROS production activates TNF-ASK1 pathway for the induction of melanoma cancer cell apoptosis. *Mal Bio Cell.* 25, 1523-1531, doi: 10.1091/mbc.E13-10-0590 (2014).

37. Wende et al., Identification of the biologically active liquid chemistry induced by a nonthermal atmospheric pressure plasma jet. *Biointerphases* 1 0, 02951801-02951816, doi: 10.1116/1.4919710 (2015).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

What is claimed is:

1. A method of therapeutic treatment of a cancerous cell in a tissue of a patient in need thereof comprising administering to the patient a cold atmospheric plasma-stimulated anti-cancer medium comprising $H_2O_2$, wherein
   (i) the medium comprises phosphate buffered saline (PBS),
   (ii) the medium is administered by transfer or injection,
   (iii) the medium has been stored between about −25° C. and about 25° C. for a period of at least 3 days prior to the treatment, and
   (iv) less than 25% of the $H_2O_2$ in the medium has decomposed during the storage period.

2. The method according to claim 1, wherein the tissue comprises lung tissue, bladder tissue, brain tissue, skin tissue, or any combination thereof.

3. The method according to claim 1, wherein the medium has been stored between about −25° C. and about 25° C. for a period of up to 7 days prior to the treatment and less than about 25% of the $H_2O_2$ in the medium has decomposed during the storage period.

4. The method according to claim 3, wherein the medium has been stored at a temperature of between about −25° C. and about 22° C., between about −25° C. and about 8° C., between about 0° C. and about 22° C., between about 0° C. and about 8° C. or between about 2° C. and about 8° C. prior to the treatment.

5. The method according to claim 1, wherein the gap between a plasma tube and the surface of the medium is decreased during the cold atmospheric plasma stimulation.

6. The method according to claim 5, wherein the gap is decreased by about 25%, about 20%, about 17%, or about 14%.

7. The method of claim 1, wherein the medium is administered by injection.

8. A method of therapeutic treatment of a cancerous cell in a tissue of a patient in need thereof comprising administering to the patient a cold atmospheric plasma-stimulated anti-cancer medium comprising $H_2O_2$, wherein
   (i) the medium comprises 3-nitro-L-tyrosine,
   (ii) the medium is administered by transfer or injection, and
   iii) the treatment is conducted at least 3 days after the cold atmospheric plasma stimulation of the anti-cancer medium.

9. The method of claim 8, wherein prior to the treatment the medium has been stored between about −25° C. and about 25° C. after the stimulation and less than 25% of the $H_2O_2$ in the medium has decomposed during the storage period.

10. The method according to claim 8, wherein the tissue comprises lung tissue, bladder tissue, brain tissue, skin tissue, or any combination thereof.

11. The method according to claim 8, wherein the medium comprises phosphate buffered saline (PBS), Dulbecco's Modified Eagle Medium (DMEM), or a combination thereof.

12. The method according to claim 8, wherein prior to the treatment the medium has been stored for up to 7 days between about −25° C. and about 25° C. after the stimulation and less than 25% of the $H_2O_2$ in the medium has decomposed during the storage period.

13. The method according to claim 12, wherein the medium has been stored at a temperature of between about −25° C. and about 22° C., between about −25° C. and about 8° C., between about 0° C. and about 22° C., between about 0° C. and about 8° C. or between about 2° C. and about 8° C. prior to the treatment.

14. The method according to claim 8, wherein when the medium comprises Dulbecco's Modified Eagle Medium (DMEM),
   (i) the medium is free of cysteine, phenylalanine and/or methionine; or
   (ii) the medium is free of phenol red.

15. The method according to claim 8, wherein a gap between the plasma tube and the surface of the media is decreased during the cold atmospheric plasma stimulation.

16. The method of claim 8, wherein the medium is administered by injection.

17. The method of claim 8, wherein the medium comprises phosphate buffered saline (PBS).

18. A method of therapeutic treatment of a cancerous cell in a tissue of a patient in need thereof comprising administering to the patient a cold atmospheric plasma-stimulated anti-cancer medium comprising $H_2O_2$, wherein
   (i) the medium comprises phosphate buffered saline (PBS),
   (ii) the medium is administered by transfer or injection, and
   (iii) the treatment is conducted at least 3 days after the cold atmospheric plasma stimulation of the anti-cancer medium.

* * * * *